United States Patent
Reddy

(10) Patent No.: US 7,238,499 B2
(45) Date of Patent: Jul. 3, 2007

(54) TRIMERIC MACROPHAGE SCAVENGER RECEPTOR FUSION PROTEINS AND ENCODING NUCLEIC ACIDS

(75) Inventor: Pranhitha Reddy, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 509 days.

(21) Appl. No.: 10/326,186

(22) Filed: Dec. 20, 2002

(65) Prior Publication Data

US 2003/0119149 A1   Jun. 26, 2003

Related U.S. Application Data

(60) Provisional application No. 60/343,315, filed on Dec. 21, 2001.

(51) Int. Cl.
| | |
|---|---|
| C07K 7/06 | (2006.01) |
| C07K 14/705 | (2006.01) |
| C07K 14/715 | (2006.01) |
| C07K 19/00 | (2006.01) |
| C12N 5/10 | (2006.01) |
| C12N 15/12 | (2006.01) |
| C12N 15/62 | (2006.01) |

(52) U.S. Cl. ............ 435/69.7; 530/300; 530/350; 530/329; 530/351; 536/23.1; 536/23.4; 536/23.5; 435/320.1; 435/325; 435/254.11; 435/252.3

(58) Field of Classification Search .......... None
See application file for complete search history.

(56) References Cited

U.S. PATENT DOCUMENTS

| | | |
|---|---|---|
| 5,716,805 A | 2/1998 | Srinivasan et al. |
| 6,087,329 A | 7/2000 | Armitage et al. |
| 6,190,886 B1 | 2/2001 | Hoppe et al. |

OTHER PUBLICATIONS

Kwon et al., Functions of newly identified members of the tumor necrosis factor receptor.ligand superfamilies in lymphocytes, Curr. Op. Immunol. 11(3):340-345, Jun. 1999.*
Gravestein et al., Tumor necrosis factor receptor family members in the immune system, Sem. Immunol. 10(6):423-434, Dec. 1998.*
Emi et al., Structure, organiztion, and chromosomal mapping of the human macrophage scavenger receptor gene, J. Biol. Chem., 268(3):2120-2125, Jan. 25, 1993.*
Matumoto et al., Human macrophage scavenger receptors: primary structure, expression, and localization in atherosclerotic lesions, Proc. Natl. Acad. Sci. USA, 87:9133-9137, Dec. 1990.*
Frank et al., Stabilization of short collagen-like triple helices by protein engineering, J. Mol. Biol. 308(5):1081-1089, May 8, 2001.*
Kishore et al., A recombinant homotrimer, composed of the alpha helical neck region of human surfactant protein D and C1q B chain globular domain, is an inhibitor of the classical complement pathway, J. Immunol. 166(1):559-565, Jan 1, 2001.*
Fanslow, et al., *Structural characteristics of CD40 ligand that determine biological function*, Seminars Immunology, 6:267-278 (1994).
Morris, et al., *Incorporation of an Isoleucine Zipper Motif Enhances the Biological Activity of Soluble CD40 (CD154)*, J. Biol. Chem., 274:418-423 (1999).
Frank, et al., *A Distinct Seven-residue Trigger Sequence Is Indispensable for Proper Coiled-coil Formation of the Human Macrophage Scavenger Receptor Oligomerization Domain*, J. Biol. Chem., 275:11672-11677 (2000).
Spencer-Green, *Etanercept (Enbrel): update on therapeutic use*, Ann. Rheum. Dis., 59 Suppl 1: 46-49 (2000).

* cited by examiner

Primary Examiner—Lorraine Spector
Assistant Examiner—Claire M. Kaufman
(74) Attorney, Agent, or Firm—Marshall, Gerstein & Borun LLP

(57) ABSTRACT

The present invention relates, in part, to a polypeptide domain having reduced immunogenicity that is capable of inducing trimers in heterologous polypeptides, fusion polypeptides comprising the trimer inducing domain, nucleic acids encoding the polypeptides of the invention and methods of making and using the same.

21 Claims, 7 Drawing Sheets

CTAGAGCTCCTGGTGAAGATTGGATTTTGCCATTCAGATTTTCTATGTTGAGC
TGCAAATCAAGCAATGTGGTATTCAAA

SR U2 (33)

AGTCCTTAATAAGTTTGAATACCACATTGCTTGATTTGCAGCTCAACATAGAA
AATCTGAATGGCAAAATCCAATCTTCACCAGGAGCT

SR U1 (32)

CTAGGTCTGACATTCTTCTGCAGCTAAGTACCTTGTTTTCCTCAGTCCAGGGA
CATGGGAATGCAATAGATGAAATCTCCA

SR L1 (35)

CTTATTAAGGACTTGGAGATTTCATCTATTGCATTCCCATGTCCCTGGACTGA
GGAAAACAAGGTACTTAGCTGCAGAAGAATGTCAGAC

CTAGGTCTGACATTCTTCTGCAGCTAAGTACCTTGTTTTCCTCAGTCCAGGGA
CATGGGAATGCAATAGATGAAATCTCCAAGTCCTTAATAAGTTTGAATACCA
CATTGCTTGATTTGCAGCTCAACATAGAAAATCTGAATGGCAAAATCCAATCT
TCACCAGGAGCTCTAG

Figure 2A

```
1/1                                              31/11
atg gcc ctg tgg atc gac agg atg caa ctc ctg tct tgc att gca cta agt ctt gca ctt
 M   A   L   W   I   D   R   M   Q   L   L   S   C   I   A   L   S   L   A   L
61/21                                            91/31
gtc aca aac agt gca cct act tca agt tct aca aag aaa aca cag cta act agg tct GAC
 V   T   N   S   A   P   T   S   S   S   T   K   K   T   Q   L   T   R   S   D
121/41                                           151/51
ATT CTT CTG CAG CTA AGT ACC TTG TTT TCC TCA GTC CAG GGA CAT GGG AAT GCA ATA GAT
 I   L   L   Q   L   S   T   L   F   S   S   V   Q   G   H   G   N   A   I   D
181/61                                           211/71
GAA ATC TCC AAG TCC TTA ATA AGT TTG AAT ACC ACA TTG CTT GAT TTG CAG CTC AAC ATA
 E   I   S   K   S   L   I   S   L   N   T   T   L   L   D   L   Q   L   N   I
241/81                                           271/91
GAA AAT CTG AAT GGC AAA ATC CAA tct tca cca gga gct cta gaa ATG CAA AAA GGT GAT
 E   N   L   N   G   K   I   Q   S   S   P   G   A   L   E   M   Q   K   G   D
301/101                                          331/111
CAG AAT CCT CAA ATT GCG GCA CAT GTC ATA AGT GAG GCC AGC AGT AAA ACA ACA TCT GTG
 Q   N   P   Q   I   A   A   H   V   I   S   E   A   S   S   K   T   T   S   V
361/121                                          391/131
TTA CAG TGG GCT GAA AAA GGA TAC TAC ACC ATG AGC AAC AAC TTG GTA ACC CTG GAA AAT
 L   Q   W   A   E   K   G   Y   Y   T   M   S   N   N   L   V   T   L   E   N
421/141                                          451/151
GGG AAA CAG CTG aCC GTT AAA AGA CAA GGA CTC TAT TAT ATC TAT GCC CAA GTC ACC TTC
 G   K   Q   L   T   V   K   R   Q   G   L   Y   Y   I   Y   A   Q   V   T   F
481/161                                          511/171
TGT TCC AAT CGG GAA GCT TCG AGT CAA GCT CCA TTT ATA GCC AGC CTC TGG CTA AAG TCC
 C   S   N   R   E   A   S   S   Q   A   P   F   I   A   S   L   W   L   K   S
541/181                                          571/191
CCC GGT AGA TTC GAG AGA ATC TTA CTC AGA GCT GCA AAT ACC ACA GTT CCC GCC AAA CCT
 P   G   R   F   E   R   I   L   L   R   A   A   N   T   H   S   S   A   K   P
601/201                                          631/211
TGC GGG CAA CAA TCC ATT CAC TTG GGA GGA GTA TTT GAA TTG CAA CCA GGT GCT TCG GTG
 C   G   Q   Q   S   I   H   L   G   G   V   F   E   L   Q   P   G   A   S   V
661/221                                          691/231
TTT GTC AAT GTG ACT GAT CCA AGC CAA GTG AGC CAT GGC ACT GGC TTC ACG TCC TTT GGC
 F   V   N   V   T   D   P   S   Q   V   S   H   G   T   G   F   T   S   F   G
721/241
TTA CTC AAA CTC TGA GcG GCc gc
 L   L   K   L   *   A   A
```

Figure 2B

```
1/1                                                     31/11
atg gct aca ggc tcc cgg acg tcc ctg ctc ctg gct ttt ggc ctg ctc tgc ctg ccc tgg
 M   A   T   G   S   R   T   S   L   L   L   A   F   G   L   L   C   L   P   W
61/21                                                   91/31
ctt caa gag ggc agt gca act agg tct GAC ATT CTT CTG CAG CTA AGT ACC TTG TTT TCC
 L   Q   E   G   S   A   T   R   S   D   I   L   L   Q   L   S   T   L   F   S
121/41                                                  151/51
TCA GTC CAG GGA CAT GGG AAT GCA ATA GAT GAA ATC TCC AAG TCC TTA ATA AGT TTG AAT
 S   V   Q   G   H   G   N   A   I   D   E   I   S   K   S   L   I   S   L   N
181/61                                                  211/71
ACC ACA TTG CTT GAT TTG CAG CTC AAC ATA GAA AAT CTG AAT GGC AAA ATC CAA tct tca
 T   T   L   L   D   L   Q   L   N   I   E   N   L   N   G   K   I   Q   S   S
241/81                                                  271/91
cca gga gct cta gaa ATG CAA AAA GGT GAT CAG AAT CCT CAA ATT GCG GCA CAT GTC ATA
 P   G   A   L   E   M   Q   K   G   D   Q   N   P   Q   I   A   A   H   V   I
301/101                                                 331/111
AGT GAG GCC AGC AGT AAA ACA ACA TCT GTG TTA CAG TGG GCT GAA AAA GGA TAC TAC ACC
 S   E   A   S   S   K   T   T   S   V   L   Q   W   A   E   K   G   Y   Y   T
361/121                                                 391/131
ATG AGC AAC AAC TTG GTA ACC CTG GAA AAT GGG AAA CAG CTG aCC GTT AAA AGA CAA GGA
 M   S   N   N   L   V   T   L   E   N   G   K   Q   L   T   V   K   R   Q   G
421/141                                                 451/151
CTC TAT TAT ATC TAT GCC CAA GTC ACC TTC TGT TCC AAT CGG GAA GCT TCG AGT CAA GCT
 L   Y   Y   I   Y   A   Q   V   T   F   C   S   N   R   E   A   S   S   Q   A
481/161                                                 511/171
CCA TTT ATA GCC AGC CTC TGG CTA AAG TCC CCC GGT AGA TTC GAG AGA ATC TTA CTC AGA
 P   F   I   A   S   L   W   L   K   S   P   G   R   F   E   R   I   L   L   R
541/181                                                 571/191
GCT GCA AAT ACC CAC AGT TCC GCC AAA CCT TGC GGG CAA CAA TCC ATT CAC TTG GGA GGA
 A   A   N   T   H   S   S   A   K   P   C   G   Q   Q   S   I   H   L   G   G
601/201                                                 631/211
GTA TTT GAA TTG CAA CCA GGT GCT TCG GTG TTT GTC AAT GTG ACT GAT CCA AGC CAA GTG
 V   F   E   L   Q   P   G   A   S   V   F   V   N   V   T   D   P   S   Q   V
661/221                                                 691/231
AGC CAT GGC ACT GGC TTC ACG TCC TTT GGC TTA CTC AAA CTC TGA GcG GCc gc
 S   H   G   T   G   F   T   S   F   G   L   L   K   L   *   A   A
```

Figure 4

```
              10         20         30         40         50
     ---------|---------|---------|---------|---------|
Query    : ATGGAGCAGTGGGATCACTTTCACAATCAACAGGAGGACACTGATAGCTG
Frame1   : M   E   Q   W   D   H   F   H   N   Q   Q   E   D   T   D   S   C 60         70         80         90        100
     ---------|---------|---------|---------|---------|
Query    : CTCCGAATCTGTGAAATTTGATGCTCGCTCAATGACAGCTTTGCTTCCTC
Frame1   : S   E   S   V   K   F   D   A   R   S   M   T   A   L   L   P   P 110        120        130        140        150
     ---------|---------|---------|---------|---------|
Query    : CGAATCCTAAAAACAGCCCTTCCCTTCAAGAGAAACTGAAGTCCTTCAAA
Frame1   : N   P   K   N   S   P   S   L   Q   E   K   L   K   S   F   K 160        170        180        190        200
     ---------|---------|---------|---------|---------|
Query    : GCTGCACTGATTGCCCTTTACCTCCTCGTGTTTGCAGTTCTCATCCCTCT
Frame1   : A   A   L   I   A   L   Y   L   L   V   F   A   V   L   I   P   L 210        220        230        240        250
     ---------|---------|---------|---------|---------|
Query    : CATTGGAATAGTGGCAGCTCAACTCCTGAAGTGGGAAACGAAGAATTGCT
Frame1   : I   G   I   V   A   A   Q   L   L   K   W   E   T   K   N   C   S 260        270        280        290        300
     ---------|---------|---------|---------|---------|
Query    : CAGTTAGTTCAACTAATGCAAATGATATAACTCAAAGTCTCACGGGAAAA
Frame1   : V   S   S   T   N   A   N   D   I   T   Q   S   L   T   G   K 310        320        330        340        350
     ---------|---------|---------|---------|---------|
Query    : GGAAATGACAGCGAAGAGGAAATGAGATTTCAAGAAGTCTTTATGGAACA
Frame1   : G   N   D   S   E   E   E   M   R   F   Q   E   V   F   M   E   H 360        370        380        390        400
     ---------|---------|---------|---------|---------|
Query    : CATGAGCAACATGGAGAAGAGAATCCAGCATATTTTAGACATGGAAGCCA
Frame1   : M   S   N   M   E   K   R   I   Q   H   I   L   D   M   E   A   N 410        420        430        440        450
     ---------|---------|---------|---------|---------|
Query    : ACCTCATGGACACAGAGCATTTCCAAAATTTCAGCATGACAACTGATCAA
Frame1   : L   M   D   T   E   H   F   Q   N   F   S   M   T   T   D   Q 460        470        480        490        500
     ---------|---------|---------|---------|---------|
Query    : AGATTTAATGACATTCTTCTGCAGCTAAGTACCTTGTTTTCCTCAGTCCA
```

Figure 4A

```
              10         20         30         40         50
         ----------|----------|----------|----------|----------|
Query  : ATGGAGCAGTGGGATCACTTTCACAATCAACAGGAGGACACTGATAGCTG
Frame1 :  M  E  Q  W  D  H  F  H  N  Q  Q  E  D  T  D  S  C 60         70         80         90        100
         ----------|----------|----------|----------|----------|
Query  : CTCCGAATCTGTGAAATTTGATGCTCGCTCAATGACAGCTTTGCTTCCTC
Frame1 :  S  E  S  V  K  F  D  A  R  S  M  T  A  L  L  P  P 110        120        130        140        150
         ----------|----------|----------|----------|----------|
Query  : CGAATCCTAAAAACAGCCCTTCCCTTCAAGAGAAACTGAAGTCCTTCAAA
Frame1 :  N  P  K  N  S  P  S  L  Q  E  K  L  K  S  F  K 160        170        180        190        200
         ----------|----------|----------|----------|----------|
Query  : GCTGCACTGATTGCCCTTTACCTCCTCGTGTTTGCAGTTCTCATCCCTCT
Frame1 :  A  A  L  I  A  L  Y  L  L  V  F  A  V  L  I  P  L 210        220        230        240        250
         ----------|----------|----------|----------|----------|
Query  : CATTGGAATAGTGGCAGCTCAACTCCTGAAGTGGGAAACGAAGAATTGCT
Frame1 :  I  G  I  V  A  A  Q  L  L  K  W  E  T  K  N  C  S 260        270        280        290        300
         ----------|----------|----------|----------|----------|
Query  : CAGTTAGTTCAACTAATGCAAATGATATAACTCAAAGTCTCACGGGAAAA
Frame1 :  V  S  S  T  N  A  N  D  I  T  Q  S  L  T  G  K 310        320        330        340        350
         ----------|----------|----------|----------|----------|
Query  : GGAAATGACAGCGAAGAGGAAATGAGATTTCAAGAAGTCTTTATGGAACA
Frame1 :  G  N  D  S  E  E  E  M  R  F  Q  E  V  F  M  E  H 360        370        380        390        400
         ----------|----------|----------|----------|----------|
Query  : CATGAGCAACATGGAGAAGAGAATCCAGCATATTTTAGACATGGAAGCCA
Frame1 :  M  S  N  M  E  K  R  I  Q  H  I  L  D  M  E  A  N 410        420        430        440        450
         ----------|----------|----------|----------|----------|
Query  : ACCTCATGGACACAGAGCATTTCCAAAATTTCAGCATGACAACTGATCAA
Frame1 :  L  M  D  T  E  H  F  Q  N  F  S  M  T  T  D  Q 460        470        480        490        500
         ----------|----------|----------|----------|----------|
Query  : AGATTTAATGACATTCTTCTGCAGCTAAGTACCTTGTTTTCCTCAGTCCA
Frame1 :  R  F  N  D  I  L  L  Q  L  S  T  L  F  S  S  V  Q 510        520        530        540        550
         ----------|----------|----------|----------|----------|
Query  : GGGACATGGGAATGCAATAGATGAAATCTCCAAGTCCTTAATAAGTTTGA
Frame1 :  G  H  G  N  A  I  D  E  I  S  K  S  L  I  S  L  N
```

```
              560        570        580        590        600
       ---------|---------|---------|---------|---------|
Query  : ATACCACATTGCTTGATTTGCAGCTCAACATAGAAAATCTGAATGGCAAA
Frame1 :   T  T  L  L  D  L  Q  L  N  I  E  N  L  N  G  K 610        620        630        640        650
       ---------|---------|---------|---------|---------|
Query  : ATCCAAGAGAATACCTTCAAACAACAAGAGGAAATCAGTAAATTAGAGGA
Frame1 :  I  Q  E  N  T  F  K  Q  Q  E  E  I  S  K  L  E  E 660        670        680        690        700
       ---------|---------|---------|---------|---------|
Query  : GCGTGTTTACAATGTATCAGCAGAAATTATGGCTATGAAAGAAGAACAAG
Frame1 :   R  V  Y  N  V  S  A  E  I  M  A  M  K  E  E  Q  V 710        720        730        740        750
       ---------|---------|---------|---------|---------|
Query  : TGCATTTGGAACAGGAAATAAAAGGAGAAGTGAAAGTACTGAATAACATC
Frame1 :  H  L  E  Q  E  I  K  G  E  V  K  V  L  N  N  I 760        770        780        790        800
       ---------|---------|---------|---------|---------|
Query  : ACTAATGATCTCAGACTGAAAGATTGGGAACATTCTCAGACCTTGAGAAA
Frame1 :   T  N  D  L  R  L  K  D  W  E  H  S  Q  T  L  R  N 810        820        830        840        850
       ---------|---------|---------|---------|---------|
Query  : TATCACTTTAATTCAAGGTCCTCCTGGACCCCCGGGTGAAAAAGGAGATC
Frame1 :  I  T  L  I  Q  G  P  P  G  P  P  G  E  K  G  D  R 860        870        880        890        900
       ---------|---------|---------|---------|---------|
Query  : GAGGTCCCACTGGAGAAAGTGGTCCACGAGGATTTCCAGGTCCAATAGGT
Frame1 :   G  P  T  G  E  S  G  P  R  G  F  P  G  P  I  G 910        920        930        940        950
       ---------|---------|---------|---------|---------|
Query  : CCTCCGGGTCTTAAAGGTGATCGGGGAGCAATTGGCTTTCCTGGAAGTCG
Frame1 :  P  P  G  L  K  G  D  R  G  A  I  G  F  P  G  S  R 960        970        980        990       1000
       ---------|---------|---------|---------|---------|
Query  : AGGACTCCCAGGATATGCCGGAAGGCCAGGAAATTCTGGACCAAAAGGCC
Frame1 :   G  L  P  G  Y  A  G  R  P  G  N  S  G  P  K  G  Q 1010       1020       1030       1040       1050
       ---------|---------|---------|---------|---------|
Query  : AGAAAGGGGAAAAGGGGAGTGGAAACACATTAAGACCAGTACAACTCACT
Frame1 :  K  G  E  K  G  S  G  N  T  L  R  P  V  Q  L  T 1060       1070
       ---------|---------|------
Query  : GATCATATTAGGGCAGGGCCCTCTTAA
Frame1 :   D  H  I  R  A  G  P  S  *
```

TRIMERIC MACROPHAGE SCAVENGER RECEPTOR FUSION PROTEINS AND ENCODING NUCLEIC ACIDS

This application claims the benefit of U.S. Provisional Application No. 60/343,315, filed Dec. 21, 2001 which is hereby incorporated by reference.

INTRODUCTION

The present invention is directed, in part, to compositions relating to polypeptide domains having reduced immunogenicity that are capable of inducing trimers in heterologous polypeptides, fusion polypeptides comprising such trimer inducing domains, nucleic acids encoding the polypeptides of the invention, and methods of making and using the same.

BACKGROUND

The structure of a polypeptide is an important element in its activity. Oftentimes, a properly folded polypeptide needs to associate with itself or different polypeptides in order to be active. Most often these interactions are as homodimers and provide an active complex, however, heterotrimers also occur. Defined trimerizing motifs are typically coiled coil domains (Burkhard et al., 2001, Trends in Cell Biol., 11:82), and includes SP-D trimerizing domains (U.S. Pat. Nos. 5,716,805 and 6,190,886).

Although lacking a distinctive coiled coil motif, additional molecules known to require trimerization for optimal activity include the tumor necrosis factor super family, such as TNF-alpha, lymphotoxin alpha, and CD40L (TNFSF5), among others. Without trimerization, many TNF super family polypeptides have low or absent activity (Fanslow et al., (1994) Seminars Immunology, 6:267–278). CD40 is a transmembrane polypeptide member of the tumor necrosis factor receptor super family and is involved in stimulating proliferation and differentiation of humoral and cellular immune cells. In particular, CD40 is involved in isotype switching and is important in T-cell activation and production of type 1 cytokines in response to protein antigens (Noelle, R, (1996) Immunity, 4:415; and Borrow et al., (1996) J. Exp. Med., 183:2129).

It has been shown that CD40L (TNFSF5) is normally active in a membrane bound form, however, this form is difficult to administer as a therapeutic. The soluble version of CD40L (TNFSF5) was found to have very little stimulatory activity, but by trimerizing soluble CD40L (TNFSF5) using a mutated GCN4 leucine zipper domain, significant activation of target cells was achieved (Fanslow et al., (1994) Seminars Immunology, 6:267–278; Morris et al., (1999) J. Biol. Chem., 274:418–423; U.S. Pat. No. 5,716, 805).

A significant limitation of using the mutant leucine zipper trimerizing domain in a therapeutic fusion polypeptide is that leucine zippers are typically nuclear proteins, i.e., intracellular. Thus even though the polypeptide may be of the same species as a subject being treated with the polypeptide, having not been seen by the immune system can lead to the polypeptide being recognized as foreign when expressed extracellularly and triggering an immune response in the subject. This response is particularly deleterious to the continuous or long-term administration of the fusion polypeptide to a patient. The present invention addresses this issue by providing polypeptide domains that will have reduced immunogenicity in addition to having trimerization properties.

SUMMARY OF THE INVENTION

The present invention relates, in part, to a polypeptide that is capable of inducing trimerization when fused to a heterologous polypeptide, fusion polypeptides comprising the trimerizing domain, nucleic acids encoding the polypeptides of the invention and methods of making and using the same. More particularly, the present invention is directed to a fusion polypeptide comprising a first polypeptide capable of forming a trimer fused to a second heterologous polypeptide having a desired biological activity. It is also contemplated that the fusion of a first polypeptide capable of forming a trimer and a second polypeptide heterologous to the first polypeptide results in an increase in the biological activity of the second polypeptide when compared to the activity of a monomer of the second polypeptide.

In one aspect, the invention encompasses a fusion polypeptide comprising a first polypeptide consisting of amino acids x to y of the polypeptide depicted in SEQ ID NO:10, wherein x is 110 to 154 and y is 201 to 270 fused to a second heterologous polypeptide, and wherein the fusion polypeptide is capable of forming a trimer.

In another aspect, the invention encompasses a fusion polypeptide comprising a first polypeptide consisting of amino acids x to y of the polypeptide depicted in SEQ ID NO: 10, wherein x is 110 to 173 and y is 179 to 270, fused to a heterologous polypeptide, and wherein the fusion polypeptide is capable of forming a trimer.

In another aspect, the invention encompasses a fusion polypeptide comprising a first polypeptide consisting of amino acids x to y of the polypeptide depicted in SEQ ID NO: 10, wherein x is 110 to 154 and y is 201 to 270, with at least one substitution of an amino acid, wherein the first polypeptide is at least 80% identical to the polypeptide depicted in SEQ ID NO: 10, and wherein said first polypeptide is fused to a second heterologous polypeptide, wherein the ability to trimerize is retained.

In another aspect, the invention encompasses a polypeptide domain comprising a first polypeptide consisting of amino acids x to y of the polypeptide depicted in SEQ ID NO:10, wherein x is 110 to 173 and y is 179 to 270, with at least one substitution of an amino acid, wherein the first polypeptide is at least 80% identical to the polypeptide depicted in SEQ ID NO: 10, wherein the ability to trimerize is retained, and wherein the first polypeptide is fused to a second heterologous polypeptide.

In yet another aspect, the invention relates to a fusion polypeptide comprising amino acids 154 to 203 of the polypeptide depicted in SEQ ID NO: 10, or alternatively, the invention relates to a fusion polypeptide comprising amino acids 120 to 180 of the polypeptide depicted in SEQ ID NO: 10.

The invention further contemplates that the polypeptide capable of forming trimer, as described above and throughout the current specification, has at least three heptad repeats. However, it is understood that the trimerization polypeptide can have four heptad repeats, five heptad repeats, six heptad repeats, seven heptad repeats or more as desired by the ordinarily skilled artisan.

In still another aspect, the invention encompasses nucleic acids encoding the polypeptides of the invention. Methods of making recombinant vectors comprising the nucleic acids of the invention are also within the scope of the invention. In yet another aspect, the polypeptides encoded by the nucleic acid molecules of the invention are non-immunogenic in a subject to which they are administered.

In addition, it is contemplated that the nucleic acids of the invention can be transfected in host cells to produce recombinant polypeptides. In another aspect, the invention encompasses a method of producing a polypeptide encoded by the nucleic acid of the invention, comprising the steps of growing a host cell transfected with nucleic acids of the invention in conditions favorable for expression of the polypeptide, and optionally isolating said polypeptide.

In yet another aspect, the invention encompasses a method of constructing a recombinant expression vector comprising the steps of linking a first nucleic acid comprising nucleotides x to y of the nucleic acid depicted in SEQ ID NO:9, wherein x is nucleotides 331 to 460, and y nucleotides is 601 to 808, and a second nucleic acid encoding a heterologous polypeptide to the first nucleic acid into a compatible cloning site of an expression vector, followed by amplifying and isolating said recombinant expression vector.

In still another aspect, the invention encompasses a method of constructing a recombinant expression vector comprising the steps of linking a first nucleic acid comprising nucleotides x to y of the nucleic acid depicted in SEQ ID NO:9, wherein x is nucleotides 331 to 508, and y nucleotides is 546 to 808, and a second nucleic acid encoding a heterologous polypeptide to the first nucleic acid into a compatible cloning site of an expression vector, followed by amplifying and isolating said recombinant expression vector.

BRIEF DESCRIPTION OF THE FIGURES

FIG. 1. Nucleic acids of the oligonucleotides utilized for construction of a polynucleotide encoding a macrophage scavenger receptor-CD40L (TNFSF5) fusion polypeptide (sequence 34 is SEQ ID NO: 1, sequence 33 is SEQ ID NO: 2, sequence 32 is SEQ ID NO: 3 and sequence 35 is SEQ ID NO: 4). The bottom sequence (SEO ID NO: 11) depicts the sequence of a construct formed by ligating sequences 32–35 together.

FIGS. 2A–B. FIG. 2A depicts the nucleic acid sequence (SEQ ID NO:5) encoding the IL2 secretion peptide fused to the scavenger receptor trimerization domain, which is fused to a receptor binding domain of the CD40L (TNFSF5). The fusion polypeptide encoded by the nucleic acid is depicted as SEQ ID NO:6. FIG. 2B depicts the nucleic acid sequence (SEQ ID NO:7) encoding the human growth hormone secretion peptide fused to the scavenger receptor trimerization domain, which is fused to a receptor binding domain of the CD40L (TNFSF5). The fusion polypeptide encoded by the nucleic acid is depicted as (SEQ ID NO:8).

FIGS. 4A–4B. The coding region of the nucleic acid (SEQ ID NO:9) encoding the human macrophage scavenger receptor A is depicted including the encoded polypeptide (SEQ ID NO:10).

DETAILED DESCRIPTION OF THE INVENTION

Figure 3:
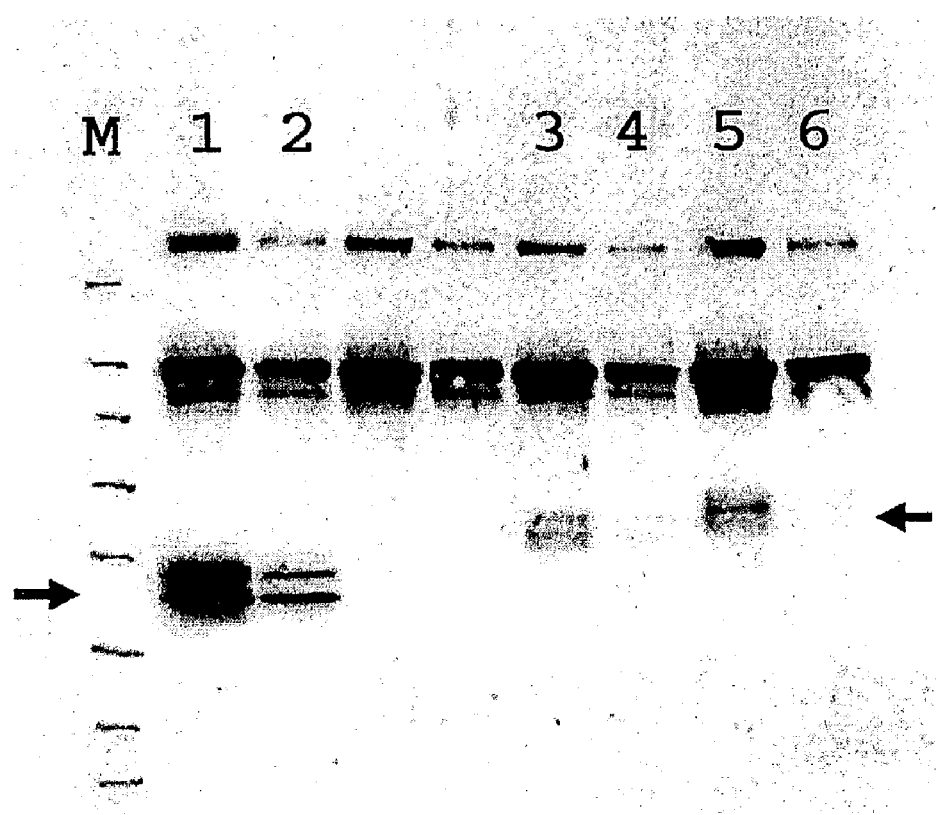
FIG. 3 depicts a western blot demonstrating expression of the CD40L (TNFSF5) fusion polypeptide. Arrows indicate the location in the gel of the fusion polypeptide. Lanes 1 and 2 are control using the isoleucine-CD40L (TNFSF5) trimerizing polypeptide, and lanes 3–6 are scavenger receptor trimerization domains fused to the receptor binding domain of CD40L (TNFSF5).

The present invention relates, in part, to a polypeptide domain capable of inducing trimers in heterologous polypeptides, fusion polypeptides comprising the trimer inducing domain, nucleic acids encoding the polypeptides, and methods of making and using the polypeptides.

In one embodiment, the invention relates to a portion of the extracellular domain of the macrophage scavenger receptor (SR-A) polypeptide corresponding to a coiled coil region, i.e., the trimerization domain. The coiled coil region of the SR-A has trimerizing properties (Frank et al., 2000, J. Biol. Chem., 275:11672–11677). As such, this domain is useful in the present invention to provide a trimerizing domain, with no or reduced immunogenicity, fused to a heterologous polypeptide.

Thus, in one embodiment, the invention relates to a fusion polypeptide comprising a first polypeptide consisting of amino acids x to y of the polypeptide depicted in SEQ ID NO: 10, wherein x is 110 to 154 and y is 201 to 270 fused to a second heterologous polypeptide. In another embodiment, the invention relates to a fusion polypeptide comprising a portion of the SR-A polypeptide consisting of amino acids x to y of the polypeptide depicted in SEQ ID NO: 10, wherein x is 110 to 173 and y is 179 to 270 fused to a second heterologous polypeptide.

In a particular embodiment, the invention relates to a fusion polypeptide comprising amino acids 154 to 203 of the polypeptide depicted in SEQ ID NO: 10 fused to a second heterologous polypeptide. In another particular embodiment, the invention relates to a fusion polypeptide comprising amino acids 120 to 180 of the polypeptide depicted in SEQ ID NO:10 fused to a second heterologous polypeptide.

In another embodiment, the invention relates to a fusion polypeptide comprising a first polypeptide consisting of amino acids x to y of the polypeptide depicted in SEQ ID NO: 10, wherein x is 110 to 154 and y is 201 to 270, with at least one substitution of an amino acid, wherein the first polypeptide is at least 80% identical to the polypeptide depicted in SEQ ID NO: 10, wherein the ability to trimerize is retained, and wherein said first polypeptide is fused to a second heterologous polypeptide. And in yet another embodiment, the invention relates to a fusion polypeptide comprising a first polypeptide consisting of amino acids x to y of the polypeptide depicted in SEQ ID NO: 10, wherein x is 110 to 173 and y is 179 to 270, with at least one substitution of an amino acid, wherein the first polypeptide is at least 80% identical to the polypeptide depicted in SEQ ID NO: 10, wherein the ability to trimerize is retained, and wherein said first polypeptide is fused to a second heterologous polypeptide.

In another embodiment, the invention relates to a fusion polypeptide comprising a first polypeptide consisting of amino acids 154 to 203 of the polypeptide depicted in SEQ ID NO: 10, with at least one substitution of an amino acid, wherein the first polypeptide is at least 80% identical to the polypeptide depicted in SEQ ID NO: 10, wherein the ability to trimerize is retained, and wherein said first polypeptide is fused to a second heterologous polypeptide. In yet another embodiment, the invention relates to a fusion polypeptide comprising a first polypeptide consisting of amino acids 154 to 203 of the polypeptide depicted in SEQ ID NO: 10, wherein said first polypeptide is fused to a second heterologous polypeptide.

In the above embodiments, the second heterologous polypeptide preferably has a desired biological activity. A biological activity, as will be understood by one of ordinary skill, can be defined as binding of a ligand to a receptor, binding of a receptor to a ligand, binding affinity of a immunoglobulin-like polypeptide to it's cognate antigen, or the like. Additionally, the biological activity may be an enzymatic activity.

In one embodiment, the fusion polypeptide the invention has reduced immunogenicity, and more preferably embodiment, the fusion polypeptide is non-immunogenic.

In one aspect, various species of macrophage scavenger receptor can serve as a trimerization motif for a fusion polypeptide, in particular, it is contemplated that bovine (Genbank Accession No. X54183), murine (Genbank Accession No. L04275), human (Genbank Accession No. XM_005021), and/or simian scavenger receptor polypeptides can be used according to the teachings of the present invention. It is to be understood that this is not an exhaustive listing and additional species' macrophage scavenger receptors are within the scope of the invention.

A consensus coiled coil polypeptide sequence, as it pertains to the invention, follows the basic pattern as set forth in Burkhard et al. (2001, Trends Cell Biol., 11:82). The positions of amino acids in the heptad repeats are typically designated alphabetically as 'a.b.c.d.e.f.g.' Positions a and d are apolar residues and there is a strong preference for specific amino acids at these positions. An apolar residue is understood by one of skill in the art to include alanine, isoleucine, glycine, proline, leucine, methionine, phenylalanine, tryptophan, valine and tyrosine. Particular residues at each of these positions can determine the nature of the secondary and tertiary structure of the coiled-coil i.e., dimeric versus trimeric. Indeed, targeted mutation has been performed to redesign dimeric leucine zippers into the trimeric isoleucine zippers by mutation of residues in positions a and d (U.S. Pat. No. 5,716,805).

Computer programs can be enlisted to assist in the identification of coiled coil polypeptides useful in the present invention. For example, FOLDER has been used to identify particular domains based on sequence identity (Srinivasan et al., (1993) Prot. Sci., 2:277–289) and can be used to identify or modify a coiled domain as used herein. Amino acids of CD40L (TNFSF5) were analyzed using folder program to study and predict trimerization propensity of several different heptad repeats within the CD40L (TNFSF5) coiled coil domains. Further, the multicoil program (Harbury et al., (1993) Science, 262:1401) can be used to confirm that a sequence, i.e., a scavenger receptor sequence such as human, murine and bovine polypeptides, are coiled coils. This program finds particular utility when a native sequence is mutated to alter the properties of a polypeptide, such as, for example to increase trimerization and/or decrease immunogenicity. Thus a mutant trimerizing polypeptide can be analyzed by computer program to determine whether it retains required characteristics.

In one embodiment, a trimerization polypeptide of the invention has at least 80% sequence identity (at least 85%, at least 90%, at least 95%, at least 97.5%, or at least 99%, and/or at least 99.5%) with a naturally occurring trimerizing polypeptide, e.g., such as the polypeptide depicted in SEQ ID NO:10, such sequence identity being determined by comparing the amino acids of the polypeptides when aligned so as to maximize overlap and identity while minimizing sequence gaps. The percent identity of two amino acids or two nucleic acids can be determined by visual inspection and mathematical calculation, or more preferably, the comparison is done by comparing sequence information using a computer program. An exemplary, preferred computer program is the Genetics Computer Group (GCG; Madison, Wis.) Wisconsin package version 10.0 program, 'GAP' (Devereux et al., (1984) Nucl. Acids Res. 12: 387). The preferred default parameters for the 'GAP' program includes: (1) The GCG implementation of a unary comparison matrix (containing a value of 1 for identities and 0 for non-identities) for nucleotides, and the weighted amino acid comparison matrix of Gribskov and Burgess, Nucl. Acids Res. 14:6745, (1986) as described by Schwartz and Dayhoff, eds., (1979) Atlas of Polypeptide Sequence and Structure, National Biomedical Research Foundation, pp. 353–358; or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps.

In one embodiment, a trimerization polypeptide of the invention comprises a sequence having at least 80% identity with amino acids x to y of the polypeptide depicted in SEQ ID NO:10, wherein x is 110 to 154 and y is 201 to 270. In another embodiment, the trimerization polypeptide of the invention comprises a sequence having at least 80% identity with amino acids x to y of the polypeptide depicted in SEQ ID NO:10, wherein x is 110 to 173 and y is 179 to 270.

Other programs used by those skilled in the art of sequence comparison can also be used, such as, for example, the BLASTN program version 2.0.9, available for use via the National Library of Medicine website www.ncbi.nlm-.nih.gov/gorf/wblast2.cgi, or the UW-BLAST 2.0 algorithm. Standard default parameter settings for UW-BLAST 2.0 are described at the following Internet site: sapiens.wustl.edul-blast/blast/#Features. In addition, the BLAST algorithm uses the BLOSUM62 amino acid scoring matix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, Analysis of compositionally biased regions in sequence databases, Methods Enzymol. 266: 554–71) or segments consisting of short-periodicity internal repeats (as determined by the XNU program of Claverie and States (Computers and Chemistry, 1993)), and (B) a statistical significance threshold for reporting matches against database sequences, or E-score (the expected probability of matches being found merely by chance, according to the stochastic model of Karlin and Altschul (1990); if the statistical significance ascribed to a match is greater than this E-score threshold, the match will not be reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

A trimerization domain can be fused to a heterologous polypeptide at the amino terminus, carboxyl terminus and/or or both. In addition, the trimerization domain can be internal to the heterologous polypeptide. Regardless of the location of the fusion of the trimerization domain and the heterologous polypeptide, it is to be understood that the trimerizing domain retains its ability to induce trimers (homotrimers and/or heterotrimers), and the heterologous polypeptide also retains its biological activity.

As used herein, the term "fusion polypeptide" refers to a contiguous polypeptide expressed from a single nucleic acid molecule, wherein the nucleic acid encodes in the same reading frame either two or more heterologous polypeptides, or domains of a polypeptide arranged in a nonnaturally occurring order. In addition to the polypeptides of the invention, other examples of fusion polypeptides include an Fc domain of an antibody or a leucine zipper domain fused to a soluble extracellular domain of a transmembrane polypeptide, e.g., CD40L (TNFSF5). WO 93/08207 and WO 96/40918 describe the preparation of oligomeric soluble forms of CD40L (TNFSF5), including an immunoglobulin fusion polypeptide and a mutated leucine zipper fusion polypeptide, respectively; the methods of constructing and assaying the products discussed therein are also applicable to the compositions of the present invention. The fusion of a trimerizing domain to a heterologous polypeptide can also occur through a linker, such as an epitope tag, or a flexible linker that assists in structural formation.

It is to be understood that any portion of a polypeptide having a desired biological activity can be expressed as a fusion to the multimerizing polypeptides of the invention. Examples include but are not limited to transmembrane polypeptides, and non-transmembrane polypeptides such as enzymes, hormones, and cytokines. In particular, it is contemplated that fusion polypeptides of GM-CSF, IL3, GM-CSF and IL3, M-CSF, and members of the hematopoietin receptor family (Cosman, et al., (1990) Trends Biochem. Sci., 15:265). Homo and hetero oligomers are further contemplated.

Additional examples of heterologous polypeptides that can be trimerized include, but are not limited to the tumor necrosis factor super family, which are listed below. Each pairing is listed first by the ligand followed by the corresponding receptor where a ligand may have more than one receptor. The nomenclature for the TNF family member symbols is as described in Locksley et al. (2001, Cell, 104:487:501), wherein a ligand is denoted by tumor necrosis factor super family (TNFSF) and receptors are denoted by tumor necrosis factor receptor super family (TNFRSF) in numerical order.

The symbol for the TNF family member ligand or receptor is first, followed by a Genbank Accession number in double parenthesis, which is followed by the various common names for the family member as applicable: TNFSFI ((Genbank Accession No. X01393), TNFB, Lymphotoxin (LT)-alpha) and its receptor tumor necrosis factor receptor TNFRSF1A ((Genbank Accession No. M75866) TNF-R); TNFSF2 ((Genbank Accession No. X02910) tumor necrosis factor (TNF)) and its receptor TNFRSF1B ((Genbank Accession No. M32315) TNF-R); TNFSF3 ((Genbank Accession No. L11016) LT-beta) and its receptor TNFRSF3 ((Genbank Accession No. L04270) LTBR, TNFR2-RP, CD18, TNFR-RP, TNFCR, TNF-R-III); TNFSF4 ((Genbank Accession No. D90224) OX-40L) and its receptor TNFRSF4 ((Genbank Accession No. X75962) OX40); TNFSF5 ((Genbank Accession No. X67878) CD40L) and its receptor TNFRSF5 ((Genbank Accession No. X60592) CD40); TNFSF6 ((Genbank Accession No. U11821) FasL) and its receptors TNFRSF6 (Genbank Accession No. M67454) FAS, CD95) and TNFRSF6B ((Genbank Accession No. AF104419) DcR3); TNFSF7 ((Genbank Accession No. L08096) CD70, CD27L) and its receptor TNFRSF7 ((Genbank Accession No. M63928) CD27); TNFSF8 ((Genbank Accession No. L09753) CD30LG) and its receptor TNFRSF8 ((Genbank Accession No. M83554) CD30); TNFSF9 ((Genbank Accession No. U03398) 4-2BB-L) and its receptor TNFRSF9 ((Genbank Accession No. L12964) 4-1BB); TNFSF10 ((Genbank Accession No. U37518) TRAIL) and its receptors TNFRSF10A ((Genbank Accession No. U90875) DR4), TNFRSF10B ((Genbank Accession No. AF012628) DR5, KILLER, TRAIL-R2), TNFRSF10C ((Genbank Accession No. AF012536) DcR1, TRAILR3), and TNFRSF10D ((Genbank Accession No. AF029761) DcR2, TRAILR4); TNFSF11 ((Genbank Accession No. AF013171) RANKL, OPGL) and its receptors TNFRSF11A ((Genbank Accession No. AF018253 RANK) and TNFRSF11B (Genbank Accession No. U94332) OPG); TNFSF12 ((Genbank Accession No. AF030099) TWEAK) and its receptors TNFRSF12 ((Genbank Accession No. U72763) DR3, TRAMP) and TNFRSF12L (DR3L); TNFSF13 ((Genbank Accession No. NM_003808) APRIL) and its receptors TNFRSF13 and TNFSF13B ((Genbank Accession No. AF136293) THANK, BLYS); TNFSF14 ((Genbank Accession No. AF036581) LIGHT, LT-gamma, HVEM-L) and its receptor TNFRSF14 ((Genbank Accession No. U70321) HVEM, ATAR, TR2, LIGHTR, HVEA); TNFSF15 ((Genbank Accession No. AF039390) TL1, VEGI) and its receptor TNFRSF15; TNFSF16 and its receptor TNFRSF16 ((Genbank Accession No. M14764) nerve growth factor receptor (NGFR), p75NTR); TNFSF17 and its receptor TNFRSF17 ((Genbank Accession No. Z29574) BCMA); TNFSF18 ((Genbank Accession No. AF125303) AITRL TL6 hGITRL) and its receptor TNFRSF18 ((Genbank Accession No. AF125304) AITR, GITR); TNFSF19 and its receptor TNFRSF19 (Genbank Accession No. AF173166); TNFSF20 and its receptor TNFRSF20 (Locksley et al., 2001, Cell, 104:487:501). In a specific embodiment, a polypeptide that can be utilized as a heterologous polypeptide by the methods and compositions of the invention is CD40L (TNFSF5).

Additional polypeptides can be fused to the fusion polypeptide to facilitate purification such as, for example, epitope tags can be placed on the amino terminus, carboxyl terminus or internally. Well known epitope tags include, e.g., histidine tag, FLAG tag, and GST among others. It is further contemplated that an epitope tag can be genetically engineered to include a proteolytic cleavage site between the tag and the rest of the polypeptide such that the epitope tag can be cleaved and removed from the fusion polypeptide. Examples of proteolytic enzymes known to recognize unique amino acids in polypeptides include Factor Xa and thrombin and are commercially available.

The invention contemplates higher order multimers of a fusion polypeptide of the invention, such that it has increased activity relative to a non-multimerized polypeptide. As used herein, a "multimer" or a "multimerized polypeptide" can include a dimer, trimer, tetramer, dimer of a trimer, trimer of a trimer, dimer of a tetramer, trimer of a tetramer and so on. Examples of additional multimerization domains can include leucine zippers or Fc domains. Accordingly, a polypeptide comprising a dimerizing domain, (e.g., an Fc domain) and trimerizing domain (e.g., a scavenger receptor alpha trimerization domain) can induce a dimer of a trimer such that six polypeptides associate. It is further contemplated that these multimers can have bioactivity that is greater than monomers or lower order multimers. For example, it is contemplated that a trimer will have higher activity than a dimer.

The terms "reduced immunogenicity" or "non-immunogenic" are understood to mean that a therapeutic, such as a polypeptide of the invention, fails to induce an appreciable immune response in a subject, preferably a human, to which it has been administered. An appreciable immune response is one that is measurable such that one of ordinary skill in the art would recognize it as having been induced by the polypeptide of the invention. This definition excludes normal variations due to differences in reagents used in the assays, variability in the samples, or where there are otherwise imperfections in the testing procedures. An immune response can be measured by any variety of standard techniques, such as for example using an enzyme linked immunosorbent assay (ELISA) to detect antibodies made in response to a therapeutic, by measuring cytokine production by the subject in appropriate time periods subsequent to administration of the polypeptide, and/or by measuring proliferation of particular immune cell types, among other well known methods.

One exemplary method of reducing or eliminating immunogenicity in a therapeutic polypeptide, is to use polypeptides derived from the same species as will be treated. For example, when a polypeptide is to be administered to a human, the polypeptide should be human derived. If in this example human polypeptides are not available, the polypeptides can be humanized such that immunogenicity is reduced. Humanizing a polypeptide can be performed, for example, in a manner analogous to humanizing antibodies, wherein a mouse antibody sequence is humanized by mutating individual amino acids to correspond to human polypeptide sequences such that the antibody does not induce a strong human anti-mouse response when administered.

Nucleic acids encoding the foregoing polypeptides are also within the scope of the invention. These nucleic acids can be cloned and mutated by well known techniques and are commonly propagated in plasmids or other vectors (Sambrook et al. eds., (1989) Molecular Cloning: A Laboratory Manual, 2nd ed., Cold Spring Harbor Laboratory, Cold Spring Harbor Laboratory Press, Cold Spring Harbor, N.Y.). Vectors can also include additional components to facilitate replication in prokaryotic and/or eukaryotic cells, integration of the construct into a eukaryotic chromosome, and markers to aid in selection of and/or screening for cells containing the construct. Vectors of the invention are recombinant DNA vectors including, but not limited to, plasmids, phages, phagemids, cosmids, viruses, retroviruses, and the like, which are used to insert heterologous polynucleotides into a cell.

As used herein, the term "linking" is understood to mean that two molecules are brought into proximity to one another by either an affinity interaction and/or a covalent attachment such as for example, ligation of nucleotides to one another in cloning, by chemical cross-linking, or by some other similar method of linking. Nucleotides can be obtained from genomic, cDNA or vector sources and linked to heterologous nucleic acids by traditional digestion and ligation in cloning, or by amplification of desired portions of sequences during PCR, among other methods.

In one embodiment, a nucleic acid molecule encoding a fusion polypeptide of the invention is operably linked to a heterologous control element. A nucleic acid is "operably linked" when it is placed into a functional relationship with another nucleic acid. Operably linked can also mean that two different nucleic acid molecules encoding different polypeptides have transcription induced simultaneously. In the case of operably linked nucleic acids, they can also be contiguous in a single transcriptional unit, while translation is directed from one or more ribosomal start sites. In addition, operably linked can mean that two polypeptide coding regions can be joined in frame such that they encode a single contiguous polypeptide, i.e., a fusion polypeptide.

An enhancer or silencer is operably linked to a nucleic acid when it is positioned relative to the nucleic acid in such a manner as to increase or decrease the transcription of the nucleic acid. Enhancers and silencers can be located upstream, downstream or embedded within the coding regions of the nucleic acid.

Expression vectors can be for expression of a fusion polypeptide of the invention in prokaryotic (e.g., *E. coli*) or eukaryotic cells (e.g., insect cells (using baculovirus expression vectors), yeast cells, plant cells, or mammalian cells). Suitable host cells include prokaryotic, eukaryotic and plant cells, and are discussed further in Goeddel, (1990) Gene Expression Technology: Methods in Enzymology 185, Academic Press, San Diego, Calif. Expression of proteins in prokaryotes is most often carried out in *E. coli* with vectors containing constitutive or inducible promoters directing the protein expression. Examples of suitable inducible *E. coli* expression vectors include pTrc (Amann et al., (1988) Gene 69:301–315) and pET 11d (Studier et al., (1990) Gene Expression Technology: Methods in Enzymology 185, Academic Press, San Diego, Calif. 60–89).

In another embodiment, the expression vector is a yeast expression vector. Examples of vectors for expression in yeast *S. cerevisiae* include pYepSec1 (Baldari et al., (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), and pPicZ (Invitrogen Corp, San Diego, Calif.). Alternatively, the expression vector is a baculovirus expression vector such as, for example, the pAc series (Smith et al. (1983) Mol. Cell Biol. 3:2156–2165). In another embodiment, a nucleic acid of the invention is expressed in mammalian cells using a mammalian expression vector. Examples of mammalian expression vectors are numerous and include but are not limited to pCDM8 (Seed (1987) Nature 329:840) and pMT2PC (Kaufman et al., (1987) EMBO J. 6:187–195).

A recombinant mammalian expression vector can also be designed such that it is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733), immunoglobulins (Banerji et al. (1983) Cell 33:729–740; Queen and Baltimore (1983) Cell 33:741–748), and mammary gland-specific promoters (e.g., milk whey promoter; U.S. Pat. No. 4,873,316 and European Application Publication No. 264,166).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic (e.g., *E. coli*), eukaryotic cell (e.g., insect cells, yeast or mammalian cells) or plant cells.

Cells used in the invention can be genetically engineered to express a fusion polypeptide of the invention. By genetically engineered is meant that the cell has been transfected, transformed or transduced with a recombinant polynucleotide molecule, and/or otherwise altered (e.g., by homologous recombination and gene activation) so as to cause the cell to express the fusion polypeptide. Methods and vectors for genetically engineering cells and/or cell lines are well known to those of skill in the art; for example, various techniques are illustrated in *Current Protocols in Molecular*

*Biology*, Ausubel et al., eds. (Wiley & Sons, New York, (1988) and quarterly updates) and Sambrook et al., (1989) *Molecular Cloning: A Laboratory Manual* (Cold Spring Laboratory Press).

It is further contemplated that the fusion polypeptides of the invention can be expressed in transgenic animals, such as for example, in mice, goats or cows. The latter example, the expression of the fusion polypeptide may be designed such that it is secreted into the animals milk. A transgenic animal can be produced by introducing the nucleic acid encoding a fusion polypeptide of the invention into a fertilized oocyte or an embryonic stem cell. Such host cells can then be used to create non-human transgenic animals.

Vector DNA can be introduced into cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals. For stable transfection of mammalian cells, it is known that, depending upon the expression vector and transfection technique used, only a small fraction of cells may integrate the transfected DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection.

In another embodiment, fusion of a trimerization polypeptide of the invention to a second heterologous polypeptide that is a ligand can result in enhanced signaling through the ligand's receptor. While not meant to be limiting, the mechanism of this increase can occur by increased binding and activation of the receptor such that the receptor has increased biological activity. For example multimerized CD40L (TNFSF5) has been shown, when administered to a cell population, to enhance immune cell proliferation relative to untreated cells (see Example, below) and also to cells that are treated with non-multimerized CD40L (TNFSF5), thus according to the invention, when soluble CD40L (TNFSF5) is fused to a trimerization polypeptide of the invention domain it has increased activity relative to soluble CD40L (TNFSF5) that is not trimerized.

The terms "enhanced" or "increased" are understood to include any measurable elevation in biological activity as measured against an untreated control. An increase can be 10%, 20%, 30%, 40% or more and increases can exceed 100% of the activity of controls. Examples of assays to measure increases include but are not limited to evaluating cytokine release, induction of surface molecule expression, increased or decreased cellular proliferation, increased or decreased apoptotic cell death, and biochemical activation, e.g., phosphorylation patterns. In a particular example, addition of trimerized CD40L (TNFSF5) to cells can result in inhibition of IL-4 induced IgE secretion or elevated expression of CD23 in mixed lymphocyte cultures. In a particular embodiment of the invention, multimers of trimers of the invention have activity that is higher than the activity of the non-multimerized trimers.

In yet another embodiment, fusion of a multimerization polypeptide, such as a trimerization domain, to a second heterologous polypeptide that is a receptor can result in decreased signaling through the corresponding, native receptor. While not meant to be limiting, the mechanism of this reduction can occur by competitive binding of the soluble polypeptide with the receptor's ligand, wherein this binding prevents the ligand from activating the receptor. For example, administration of TNFR:Fc (i.e., Etanercept), a dimer, results in a reduction in the signaling through the TNF-alpha receptor relative to untreated cells as measured, in part, by reduced disease symptoms (Spencer-Green, 2000, Ann. Rheum. Dis., 59 Suppl 1, pp. 46–9). Thus, a multimer of a TNFR according to the invention can inhibit TNF-alpha mediated inflammation.

The term "reduced" is understood to include any measurable decrease in biological activity as measured against an untreated control. More particularly, a decrease can be 10%, 20% or more including up to an 100% reduction. Examples of assays to measure this reduction include but are not limited to increased or decreased cytokine release, induction of surface molecule expression, increased or decreased cellular proliferation, increased or decreased apoptotic cell death, and biochemical activation, e.g., phosphorylation patterns.

The activity of the fusion polypeptide is partly determined by its affinity to a binding partner (e.g., receptor or ligand). The affinity of the trimerized molecules for their respective binding partner can be measured using biospecific interaction analysis (BIA), which is a biosensor, i.e., an instrument that combines a biological recognition mechanism with a sensing device or transducer. An exemplary biosensor is BIOcore™ (Pharmacia). This uses the optical phenomenon surface plasmon resonance to monitor the interaction between two biological molecules. Molecule pairs having affinity constants in the range of $10^5$ to $10^{10}$ $M^{-1}$, and association rate constants in the range of $10^3$ to $10^6$ $M^{-1}s^{-1}$ are suited for this method.

It is also contemplated that, as trimers (or higher order multimers) have more binding sites for their binding partner than dimers or monomers, the multimerized polypeptides of the invention will also have higher avidity for binding partners than will monomers or dimers (or lower order multimers). This higher degree of avidity increases the specific binding of the multimers to their binding partners. As such, in one embodiment, it is contemplated that the polypeptides of the invention can be linked to heterologous therapeutic molecules for high efficiency delivery to target cells expressing a binding partner. Examples of heterologous molecules that can be linked include, but are not limited to, radioactive moieties, e.g., $I^{125}$, $Y^{90}$, and/or polypeptide toxins, e.g., ricin, botulism toxin. The linkage can be through standard cross linking techniques well known in the art.

Pharmaceutical Preparations and Methods of Administration

The polypeptides of the invention can be formulated as compounds suitable for administration to a patient in need of treatment. Such compounds are useful in treating immune related disorders and/or in increasing the stimulation of an otherwise normal immune response. A therapeutically effective dose refers to that amount of the compound sufficient to result in amelioration of symptoms of, for example, immunodeficiency or inflammatory conditions or diseases. Furthermore, when a polypeptide of the invention is co-administered with another therapeutic agent, doses are modified according to any interactions that may occur between the therapeutic agents.

Effective Dose

Toxicity and therapeutic efficacy of compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred.

While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture prior to administration to a patient.

When another therapeutic is administered in combination with the polypeptides of the invention (coadministration), the polypeptides of the invention can be delivered either prior to, simultaneous with, or after delivery of the second therapeutic. Simultaneous administration encompasses mixing the polypeptides of the invention with the second therapeutic prior to administration to the patient, or administration to the patient in separate infusions, albeit at the same time. It is also contemplated that the dose of the second therapeutic should be consistent with established therapeutic ranges, however, should there can be an increase in effectiveness of the therapeutic when used in combination with a polypeptides of the invention that is greater than the sum of either alone there is synergy. Thus, in the case of synergy, it will be understood that doses can be decreased relative to recommended ranges in light of enhanced effectiveness.

In one embodiment of the invention, a polypeptide of the invention is administered one time per week to treat the various medical disorders disclosed herein, in another embodiment is administered at least two times per week, and in another embodiment is administered at least once per day. An adult patient is a person who is 18 years of age or older. If injected, the effective amount, per adult dose, of a polypeptide of the invention ranges from about 1–500 mg/m$^2$, or from about 1–200 mg/m$^2$, or from about 1–40 mg/m$^2$ or about 5–25 mg/m$^2$. Alternatively, a flat dose may be administered, whose amount may range from 2–500 mg/dose, 2–100 mg/dose or from about 10–80 mg/dose. If the dose is to be administered more than one time per week, an exemplary dose range is the same as the foregoing described dose ranges or lower. Preferably, polypeptides of the invention are administered two or more times per week at a per dose range of 25–100 mg/dose.

In one embodiment of the invention, the various indications described below are treated by administering a preparation acceptable for injection containing a polypeptide of the invention at 80–100 mg/dose, or alternatively, containing 80 mg per dose. The dose can be administered at biweekly, weekly doses, or separated by several weeks (for example 2 to 8).

If a route of administration of the polypeptides of the invention other than injection is used, the dose is appropriately adjusted in accord with standard medical practices. For example, if the route of administration is inhalation, dosing may be one to seven times per week at dose ranges from 10 mg/dose to 50 mg per dose.

In many instances, an improvement in a patient's condition will be obtained by injecting a dose of up to about 100 mg of the polypeptides of the invention one to three times per week over a period of at least three weeks, though treatment for longer periods may be necessary to induce the desired degree of improvement. For incurable chronic conditions, for example, patients with bone marrow failure caused by a genetic disorder, the regimen may be continued indefinitely.

For pediatric patients (ages 4–17), a suitable regimen involves the subcutaneous injection of 0.4 mg/kg to 5 mg/kg of a the polypeptides of the invention, administered by subcutaneous injection one or more times per week.

Formulations and Use

Pharmaceutical compositions for use of the compositions of the present invention may be formulated in conventional manner using one or more physiologically acceptable carriers or excipients. Thus, the compounds and their physiologically acceptable salts and solvates may be formulated for administration by inhalation or insufflation (either through the mouth or the nose) or buccal, parenteral or rectal administration.

For buccal administration the compositions may take the form of tablets or lozenges formulated in conventional manner.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated for injection. Such formulations are typically stored as aqueous solutions that can be frozen and thawed, but can be also be prepared as lyophilized samples for extended storage. These formulations are frequently presented in a solution that is isotonic with human blood, namely, about 150 mM and buffered. Common buffers include sodium phosphate and sodium acetate and the pH range can be from 1 to 14, but is more typically around 4.5 to 6. These formulations also can have a polyol (e.g., sorbitol, trehalose, sucrose, etc.) and a surfactant (e.g., polysorbate, Tween 80, etc.) and do not require sodium chloride to isotonic in solution.

The polypeptides of the invention can also be formulated as a depot preparation. Such long acting formulations may be administered by implantation (for example subcutaneously or intramuscularly) or by intramuscular injection.

Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

EXAMPLES

Cloning

Constructs were made by linking three different nucleic acids: 1) the receptor binding domain (RBD) of human CD40L (TNFSF5) as a 0.4kb XbaI-NotI previously fused to a CD40L (TNFSF5)194W deletion as described in Morris et al. (1999, J. Biol. Chem., 274:418–423); 2) the scavenger receptor trimerization sequence AvrII-XbaI fragment generated as described below; 3) and the 5.6 kb SpeI-NotI fragment consisting of the pSMAG expression vector containing the signal sequences and the transcriptional promoter. The resulting nucleic acids are depicted in SEQ ID NOs:5 and 7.

The AvrII-XbaI fragment consisting of the 7 heptad repeat from the scavenger receptor coding sequence were generated through hybridization and ligation of two sets of synthetic oligonucleotides shown in FIG. 1 (SR oligo sequences). The oligonucleotide sequence was designed to contain AvrII restriction site overhang at the 5' end and the XbaI restriction site overhang (compatible sequence) at the 3' end of the synthetic scavenger receptor fragment. The XbaI site is TCTAGA, the AvrII restriction site is C/CTAGG and the SpeI restriction site is A/CTAGT. Ligation of SpeI to AvrII generates the sequence ACTAGG encoding amino acids threonine and arginine respectively (single amino acid letter code T and R).

Oligos 33 (SEQ ID NO: 2) and 35 (SEQ ID NO: 4) were phosphorylated using T4 polynucleotide kinase and ATP at 37° C. for 1 hour. The appropriate oligonucleotide preparations were mixed together in two separate reaction vessels (eppendorf tubes) at 2 μg/ml concentration and annealed by heating each oligonucleotide pair to 95° C for 2 minutes and then held at 65° C. for 3 minutes and allowed to cool gradually to room temperature (25° C.) over 45 minutes. Oligo 32 (SEQ ID NO:3) was annealed to complementary oligo 35 and Oligo 33 was annealed to complementary oligo 34 (SEQ ID NO: 1). The two sets of reactions were mixed together and ligated for 1 hour using DNA Ligase. (See SEQ ID NO: 11). The ligation reaction was analyzed using preparative 3% Nusieve® agarose gel electrophoresis and the approximately 150 basepairs fragment corresponding to the scavenger receptor AvrII/XbaI fragment was visualized and isolated from the gel.

These nucleic acids were cloned upstream (i.e., N-terminal end) of the receptor binding domain (RBD) of CD40L (TNFSF5) by ligating to an XbaI/NotI fragment containing the CD40L (TNFSF5) RBD and a NotI/SpeI fragment containing the pSMAG vector and the signal sequence. These scavenger receptor nucleic acids replaced the nucleic acids encoding the mutein leucine zipper that were previously used to trimerize/stabilize the trimers of soluble CD40L (TNFSF5). The expression vector pSMAG used for these constructs contained the transcriptional promoter and either the IL2 signal sequence or the human growth hormone (GH) signal sequence to enable secretion of CD40L (TNFSF5).

The nucleic acid of the final constructs was analyzed on an automated sequencer. Sequence from the signal sequence through the junction of the RBD of CD40L (TNFSF5) was obtained to confirm correct ligation. FIG. 2A depicts a fusion polypeptide of the invention where amino acids 1 to 24 are the IL2 signal peptide, amino acids 25 to 39 are linker sequences, amino acids 40 to 88 are the trimerization domain, amino acids 89 to 95 are linker sequences and amino acids 96 to 244 are the CD40L (TNFSF5) 194W deletion sequences and FIG. 2B depicts a fusion polypeptide of the invention where amino acids 1 to 25 are the IL2 signal peptide, amino acids 26 to 29 are linker sequences, amino acids 30 to 78 are the trimerization domain, amino acids 79 to 85 are linker sequences and amino acids 86 to 234 are the CD40L (TNFSF5) 194W deletion sequences.

Expression

COS cells were transfected with plasmid DNA with 2 μg in each well in a 6 well transfection vessel and the growth/conditioned media was harvested after 3 days and analyzed on SDS PAGE western blots using a polyclonal anti CD40L (TNFSF5) antibody. The resulting western blot, shown in FIG. 3, demonstrates that both isoleucine zipper CD40L (TNFSF5) (Morris et al., (1999) J. Biol. Chem., 274:418–423) and the two forms of the scavenger receptor (SR)-CD40L (TNFSF5), described above, are expressed and secreted. Lanes 1, 3 and 5 contain harvest supernatant at 1:10 dilution and lanes 2, 4 and 6 contain supernatant at 1:30 dilution. Lanes contain harvest supernatant from cells transfected as follows: lanes 1 and 2 contain isoleucine zipper CD40L (TNFSF5) cDNA, lanes 4 and 6 contain growth hormone signal sequence linked to the scavenger receptor trimerization domain-CD40L (TNFSF5) (GH-SR-CD40L), lanes 5 and 6 contain IL2 signal sequence linked to the scavenger receptor trimerization domain-CD40L (TNFSF5) (IL2-SR-CD40L).

Bioactivity

The transfection harvest media was analyzed for bioactivity in a B cell proliferation bioassay as described by Morris et al. (1999, J. Biol. Chem., 274:418–423). Costimulation of human blood B cell proliferation was assessed by culturing T-cell depleted PBMC (E) in round bottom 96 well microtiter plates (1×10$^5$ cells in 200 μl) for 4 days in the presence of a titration of huCD40L (TNFSF5). Cells were pulsed with tritiated thymidine (91 μci/well) for the final 18 hr culture period. Cells cultured with 1 μg/ml of isoleucine zipper CD40L (TNFSF5) were included as a positive control. Control cells were included as negative control. B cells are the only cells in the E prep that will proliferate in response to CD40L (TNFSF5). The results demonstrate that transfection supernatants containing the scavenger receptor trimerization domain fused to RBD of CD40L (TNFSF5), with the growth hormone signal sequence, are about as active as the leucine zipper form of the CD40L (TNFSF5).

Equivalents and References

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

---

SEQUENCE LISTING

<160> NUMBER OF SEQ ID NOS: 10

<210> SEQ ID NO 1
<211> LENGTH: 80
<212> TYPE: DNA
<213> ORGANISM: Homo sapiens

<400> SEQUENCE: 1
ctagagctcc tggtgaagat tggattttgc cattcagatt ttctatgttg agctgcaaat    60
caagcaatgt ggtattcaaa                                                80

<210> SEQ ID NO 2
<211> LENGTH: 89
<212> TYPE: DNA
<213> ORGANISM: Homo sapiens

<400> SEQUENCE: 2
agtccttaat aagtttgaat accacattgc ttgatttgca gctcaacata gaaaatctga    60
atggcaaaat ccaatcttca ccaggagct                                      89

<210> SEQ ID NO 3
<211> LENGTH: 81
<212> TYPE: DNA
<213> ORGANISM: Homo sapiens

<400> SEQUENCE: 3
ctaggtctga cattcttctg cagctaagta ccttgttttc ctcagtccag ggacatggga    60
atgcaataga tgaaatctcc a                                              81

<210> SEQ ID NO 4
<211> LENGTH: 90
<212> TYPE: DNA
<213> ORGANISM: Homo sapiens

<400> SEQUENCE: 4
cttattaagg acttggagat ttcatctatt gcattcccat gtccctggac tgaggaaaac    60
aaggtactta gctgcagaag aatgtcagac                                     90

<210> SEQ ID NO 5
<211> LENGTH: 1077
<212> TYPE: DNA
<213> ORGANISM: Homo sapiens
<220> FEATURE:
<221> NAME/KEY: CDS
<222> LOCATION: (1)..(1077)
<223> OTHER INFORMATION:

<400> SEQUENCE: 5 atg gag cag tgg gat cac ttt cac aat caa cag gag gac act gat agc    48
Met Glu Gln Trp Asp His Phe His Asn Gln Gln Glu Asp Thr Asp Ser
1               5                   10                  15

```
tgc tcc gaa tct gtg aaa ttt gat gct cgc tca atg aca gct ttg ctt       96
Cys Ser Glu Ser Val Lys Phe Asp Ala Arg Ser Met Thr Ala Leu Leu
         20                  25                  30 cct ccg aat cct aaa aac agc cct tcc ctt caa gag aaa ctg aag tcc      144
Pro Pro Asn Pro Lys Asn Ser Pro Ser Leu Gln Glu Lys Leu Lys Ser
     35                  40                  45 ttc aaa gct gca ctg att gcc ctt tac ctc ctc gtg ttt gca gtt ctc      192
Phe Lys Ala Ala Leu Ile Ala Leu Tyr Leu Leu Val Phe Ala Val Leu
 50                  55                  60 atc cct ctc att gga ata gtg gca gct caa ctc ctg aag tgg gaa acg      240
Ile Pro Leu Ile Gly Ile Val Ala Ala Gln Leu Leu Lys Trp Glu Thr
 65                  70                  75                  80 aag aat tgc tca gtt agt tca act aat gca aat gat ata act caa agt      288
Lys Asn Cys Ser Val Ser Ser Thr Asn Ala Asn Asp Ile Thr Gln Ser
             85                  90                  95 ctc acg gga aaa gga aat gac agc gaa gag gaa atg aga ttt caa gaa      336
Leu Thr Gly Lys Gly Asn Asp Ser Glu Glu Glu Met Arg Phe Gln Glu
            100                 105                 110 gtc ttt atg gaa cac atg agc aac atg gag aag aga atc cag cat att      384
Val Phe Met Glu His Met Ser Asn Met Glu Lys Arg Ile Gln His Ile
        115                 120                 125 tta gac atg gaa gcc aac ctc atg gac aca gag cat ttc caa aat ttc      432
Leu Asp Met Glu Ala Asn Leu Met Asp Thr Glu His Phe Gln Asn Phe
130                 135                 140 agc atg aca act gat caa aga ttt aat gac att ctt ctg cag cta agt      480
Ser Met Thr Thr Asp Gln Arg Phe Asn Asp Ile Leu Leu Gln Leu Ser
145                 150                 155                 160 acc ttg ttt tcc tca gtc cag gga cat ggg aat gca ata gat gaa atc      528
Thr Leu Phe Ser Ser Val Gln Gly His Gly Asn Ala Ile Asp Glu Ile
                165                 170                 175 tcc aag tcc tta ata agt ttg aat acc aca ttg ctt gat ttg cag ctc      576
Ser Lys Ser Leu Ile Ser Leu Asn Thr Thr Leu Leu Asp Leu Gln Leu
            180                 185                 190 aac ata gaa aat ctg aat ggc aaa atc caa gag aat acc ttc aaa caa      624
Asn Ile Glu Asn Leu Asn Gly Lys Ile Gln Glu Asn Thr Phe Lys Gln
        195                 200                 205 caa gag gaa atc agt aaa tta gag gag cgt gtt tac aat gta tca gca      672
Gln Glu Glu Ile Ser Lys Leu Glu Glu Arg Val Tyr Asn Val Ser Ala
    210                 215                 220 gaa att atg gct atg aaa gaa gaa caa gtg cat ttg gaa cag gaa ata      720
Glu Ile Met Ala Met Lys Glu Glu Gln Val His Leu Glu Gln Glu Ile
225                 230                 235                 240 aaa gga gaa gtg aaa gta ctg aat aac atc act aat gat ctc aga ctg      768
Lys Gly Glu Val Lys Val Leu Asn Asn Ile Thr Asn Asp Leu Arg Leu
                245                 250                 255 aaa gat tgg gaa cat tct cag acc ttg aga aat atc act tta att caa      816
Lys Asp Trp Glu His Ser Gln Thr Leu Arg Asn Ile Thr Leu Ile Gln
            260                 265                 270 ggt cct cct gga ccc ccg ggt gaa aaa gga gat cga ggt ccc act gga      864
Gly Pro Pro Gly Pro Pro Gly Glu Lys Gly Asp Arg Gly Pro Thr Gly
        275                 280                 285 gaa agt ggt cca cga gga ttt cca ggt cca ata ggt cct ccg ggt ctt      912
Glu Ser Gly Pro Arg Gly Phe Pro Gly Pro Ile Gly Pro Pro Gly Leu
    290                 295                 300 aaa ggt gat cgg gga gca att ggc ttt cct gga agt cga gga ctc cca      960
Lys Gly Asp Arg Gly Ala Ile Gly Phe Pro Gly Ser Arg Gly Leu Pro
305                 310                 315                 320 gga tat gcc gga agg cca gga aat tct gga cca aaa ggc cag aaa ggg     1008
Gly Tyr Ala Gly Arg Pro Gly Asn Ser Gly Pro Lys Gly Gln Lys Gly
```

```
                    325                 330                 335
gaa aag ggg agt gga aac aca tta aga cca gta caa ctc act gat cat    1056
Glu Lys Gly Ser Gly Asn Thr Leu Arg Pro Val Gln Leu Thr Asp His
        340                 345                 350 att agg gca ggg ccc tct taa                                        1077
Ile Arg Ala Gly Pro Ser
        355
```

<210> SEQ ID NO 6
<211> LENGTH: 358
<212> TYPE: PRT
<213> ORGANISM: Homo sapiens

<400> SEQUENCE: 6

```
Met Glu Gln Trp Asp His Phe His Asn Gln Gln Glu Asp Thr Asp Ser
1               5                   10                  15

Cys Ser Glu Ser Val Lys Phe Asp Ala Arg Ser Met Thr Ala Leu Leu
            20                  25                  30

Pro Pro Asn Pro Lys Asn Ser Pro Ser Leu Gln Glu Lys Leu Lys Ser
        35                  40                  45

Phe Lys Ala Ala Leu Ile Ala Leu Tyr Leu Leu Val Phe Ala Val Leu
50                  55                  60

Ile Pro Leu Ile Gly Ile Val Ala Ala Gln Leu Leu Lys Trp Glu Thr
65                  70                  75                  80

Lys Asn Cys Ser Val Ser Ser Thr Asn Ala Asn Asp Ile Thr Gln Ser
                85                  90                  95

Leu Thr Gly Lys Gly Asn Asp Ser Glu Glu Met Arg Phe Gln Glu
            100                 105                 110

Val Phe Met Glu His Met Ser Asn Met Glu Lys Arg Ile Gln His Ile
        115                 120                 125

Leu Asp Met Glu Ala Asn Leu Met Asp Thr Glu His Phe Gln Asn Phe
130                 135                 140

Ser Met Thr Thr Asp Gln Arg Phe Asn Asp Ile Leu Leu Gln Leu Ser
145                 150                 155                 160

Thr Leu Phe Ser Ser Val Gln Gly His Gly Asn Ala Ile Asp Glu Ile
                165                 170                 175

Ser Lys Ser Leu Ile Ser Leu Asn Thr Thr Leu Leu Asp Leu Gln Leu
            180                 185                 190

Asn Ile Glu Asn Leu Asn Gly Lys Ile Gln Glu Asn Thr Phe Lys Gln
        195                 200                 205

Gln Glu Glu Ile Ser Lys Leu Glu Arg Val Tyr Asn Val Ser Ala
210                 215                 220

Glu Ile Met Ala Met Lys Glu Glu Gln Val His Leu Glu Gln Glu Ile
225                 230                 235                 240

Lys Gly Glu Val Lys Val Leu Asn Asn Ile Thr Asn Asp Leu Arg Leu
                245                 250                 255

Lys Asp Trp Glu His Ser Gln Thr Leu Arg Asn Ile Thr Leu Ile Gln
            260                 265                 270

Gly Pro Pro Gly Pro Pro Gly Glu Lys Gly Asp Arg Gly Pro Thr Gly
        275                 280                 285

Glu Ser Gly Pro Arg Gly Phe Pro Gly Pro Ile Gly Pro Pro Gly Leu
        290                 295                 300

Lys Gly Asp Arg Gly Ala Ile Gly Phe Pro Gly Ser Arg Gly Leu Pro
305                 310                 315                 320

Gly Tyr Ala Gly Arg Pro Gly Asn Ser Gly Pro Lys Gly Gln Lys Gly
```

```
                          325                 330                 335
Glu Lys Gly Ser Gly Asn Thr Leu Arg Pro Val Gln Leu Thr Asp His
            340                 345                 350

Ile Arg Ala Gly Pro Ser
        355

<210> SEQ ID NO 7
<211> LENGTH: 743
<212> TYPE: DNA
<213> ORGANISM: Homo sapiens
<220> FEATURE:
<221> NAME/KEY: CDS
<222> LOCATION: (1)..(735)
<223> OTHER INFORMATION:

<400> SEQUENCE: 7 atg gcc ctg tgg atc gac agg atg caa ctc ctg tct tgc att gca cta     48
Met Ala Leu Trp Ile Asp Arg Met Gln Leu Leu Ser Cys Ile Ala Leu
1               5                   10                  15 agt ctt gca ctt gtc aca aac agt gca cct act tca agt tct aca aag     96
Ser Leu Ala Leu Val Thr Asn Ser Ala Pro Thr Ser Ser Ser Thr Lys
            20                  25                  30 aaa aca cag cta act agg tct gac att ctt ctg cag cta agt acc ttg    144
Lys Thr Gln Leu Thr Arg Ser Asp Ile Leu Leu Gln Leu Ser Thr Leu
        35                  40                  45 ttt tcc tca gtc cag gga cat ggg aat gca ata gat gaa atc tcc aag    192
Phe Ser Ser Val Gln Gly His Gly Asn Ala Ile Asp Glu Ile Ser Lys
    50                  55                  60 tcc tta ata agt ttg aat acc aca ttg ctt gat ttg cag ctc aac ata    240
Ser Leu Ile Ser Leu Asn Thr Thr Leu Leu Asp Leu Gln Leu Asn Ile
65                  70                  75                  80 gaa aat ctg aat ggc aaa atc caa tct tca cca gga gct cta gaa atg    288
Glu Asn Leu Asn Gly Lys Ile Gln Ser Ser Pro Gly Ala Leu Glu Met
                85                  90                  95 caa aaa ggt gat cag aat cct caa att gcg gca cat gtc ata agt gag    336
Gln Lys Gly Asp Gln Asn Pro Gln Ile Ala Ala His Val Ile Ser Glu
            100                 105                 110 gcc agc agt aaa aca aca tct gtg tta cag tgg gct gaa aaa gga tac    384
Ala Ser Ser Lys Thr Thr Ser Val Leu Gln Trp Ala Glu Lys Gly Tyr
        115                 120                 125 tac acc atg agc aac aac ttg gta acc ctg gaa aat ggg aaa cag ctg    432
Tyr Thr Met Ser Asn Asn Leu Val Thr Leu Glu Asn Gly Lys Gln Leu
    130                 135                 140 acc gtt aaa aga caa gga ctc tat tat atc tat gcc caa gtc acc ttc    480
Thr Val Lys Arg Gln Gly Leu Tyr Tyr Ile Tyr Ala Gln Val Thr Phe
145                 150                 155                 160 tgt tcc aat cgg gaa gct tcg agt caa gct cca ttt ata gcc agc ctc    528
Cys Ser Asn Arg Glu Ala Ser Ser Gln Ala Pro Phe Ile Ala Ser Leu
                165                 170                 175 tgg cta aag tcc ccc ggt aga ttc gag aga atc tta ctc aga gct gca    576
Trp Leu Lys Ser Pro Gly Arg Phe Glu Arg Ile Leu Leu Arg Ala Ala
            180                 185                 190 aat acc cac agt tcc gcc aaa cct tgc ggg caa caa tcc att cac ttg    624
Asn Thr His Ser Ser Ala Lys Pro Cys Gly Gln Gln Ser Ile His Leu
        195                 200                 205 gga gga gta ttt gaa ttg caa cca ggt gct tcg gtg ttt gtc aat gtg    672
Gly Gly Val Phe Glu Leu Gln Pro Gly Ala Ser Val Phe Val Asn Val
    210                 215                 220 act gat cca agc caa gtg agc cat ggc act ggc ttc acg tcc ttt ggc    720
Thr Asp Pro Ser Gln Val Ser His Gly Thr Gly Phe Thr Ser Phe Gly
225                 230                 235                 240
```

```
tta ctc aaa ctc tga gcggccgc                                      743
Leu Leu Lys Leu
```

<210> SEQ ID NO 8
<211> LENGTH: 244
<212> TYPE: PRT
<213> ORGANISM: Homo sapiens

<400> SEQUENCE: 8

```
Met Ala Leu Trp Ile Asp Arg Met Gln Leu Ser Cys Ile Ala Leu
1               5                   10                  15

Ser Leu Ala Leu Val Thr Asn Ser Ala Pro Thr Ser Ser Thr Lys
                20                  25                  30

Lys Thr Gln Leu Thr Arg Ser Asp Ile Leu Leu Gln Leu Ser Thr Leu
            35                  40                  45

Phe Ser Ser Val Gln Gly His Gly Asn Ala Ile Asp Glu Ile Ser Lys
    50                  55                  60

Ser Leu Ile Ser Leu Asn Thr Thr Leu Leu Asp Leu Gln Leu Asn Ile
65                  70                  75                  80

Glu Asn Leu Asn Gly Lys Ile Gln Ser Ser Pro Gly Ala Leu Glu Met
                85                  90                  95

Gln Lys Gly Asp Gln Asn Pro Gln Ile Ala Ala His Val Ile Ser Glu
            100                 105                 110

Ala Ser Ser Lys Thr Thr Ser Val Leu Gln Trp Ala Glu Lys Gly Tyr
        115                 120                 125

Tyr Thr Met Ser Asn Asn Leu Val Thr Leu Glu Asn Gly Lys Gln Leu
    130                 135                 140

Thr Val Lys Arg Gln Gly Leu Tyr Tyr Ile Tyr Ala Gln Val Thr Phe
145                 150                 155                 160

Cys Ser Asn Arg Glu Ala Ser Ser Gln Ala Pro Phe Ile Ala Ser Leu
                165                 170                 175

Trp Leu Lys Ser Pro Gly Arg Phe Glu Arg Ile Leu Leu Arg Ala Ala
            180                 185                 190

Asn Thr His Ser Ser Ala Lys Pro Cys Gly Gln Gln Ser Ile His Leu
        195                 200                 205

Gly Gly Val Phe Glu Leu Gln Pro Gly Ala Ser Val Phe Val Asn Val
    210                 215                 220

Thr Asp Pro Ser Gln Val Ser His Gly Thr Gly Phe Thr Ser Phe Gly
225                 230                 235                 240

Leu Leu Lys Leu
```

<210> SEQ ID NO 9
<211> LENGTH: 713
<212> TYPE: DNA
<213> ORGANISM: Homo sapiens
<220> FEATURE:
<221> NAME/KEY: CDS
<222> LOCATION: (1)..(705)
<223> OTHER INFORMATION:

<400> SEQUENCE: 9

```
atg gct aca ggc tcc cgg acg tcc ctg ctc ctg gct ttt ggc ctg ctc      48
Met Ala Thr Gly Ser Arg Thr Ser Leu Leu Leu Ala Phe Gly Leu Leu
1               5                   10                  15 tgc ctg ccc tgg ctt caa gag ggc agt gca act agg tct gac att ctt      96
Cys Leu Pro Trp Leu Gln Glu Gly Ser Ala Thr Arg Ser Asp Ile Leu
                20                  25                  30
```

| | |
|---|---|
| ctg cag cta agt acc ttg ttt tcc tca gtc cag gga cat ggg aat gca<br>Leu Gln Leu Ser Thr Leu Phe Ser Ser Val Gln Gly His Gly Asn Ala<br>35                          40                    45 | 144 |
| ata gat gaa atc tcc aag tcc tta ata agt ttg aat acc aca ttg ctt<br>Ile Asp Glu Ile Ser Lys Ser Leu Ile Ser Leu Asn Thr Thr Leu Leu<br>50                          55                    60 | 192 |
| gat ttg cag ctc aac ata gaa aat ctg aat ggc aaa atc caa tct tca<br>Asp Leu Gln Leu Asn Ile Glu Asn Leu Asn Gly Lys Ile Gln Ser Ser<br>65                 70                    75                    80 | 240 |
| cca gga gct cta gaa atg caa aaa ggt gat cag aat cct caa att gcg<br>Pro Gly Ala Leu Glu Met Gln Lys Gly Asp Gln Asn Pro Gln Ile Ala<br>                      85                    90                    95 | 288 |
| gca cat gtc ata agt gag gcc agc agt aaa aca aca tct gtg tta cag<br>Ala His Val Ile Ser Glu Ala Ser Ser Lys Thr Thr Ser Val Leu Gln<br>                  100                 105               110 | 336 |
| tgg gct gaa aaa gga tac tac acc atg agc aac aac ttg gta acc ctg<br>Trp Ala Glu Lys Gly Tyr Tyr Thr Met Ser Asn Asn Leu Val Thr Leu<br>               115                 120               125 | 384 |
| gaa aat ggg aaa cag ctg acc gtt aaa aga caa gga ctc tat tat atc<br>Glu Asn Gly Lys Gln Leu Thr Val Lys Arg Gln Gly Leu Tyr Tyr Ile<br>130                       135                 140 | 432 |
| tat gcc caa gtc acc ttc tgt tcc aat cgg gaa gct tcg agt caa gct<br>Tyr Ala Gln Val Thr Phe Cys Ser Asn Arg Glu Ala Ser Ser Gln Ala<br>145                       150                 155               160 | 480 |
| cca ttt ata gcc agc ctc tgg cta aag tcc ccc ggt aga ttc gag aga<br>Pro Phe Ile Ala Ser Leu Trp Leu Lys Ser Pro Gly Arg Phe Glu Arg<br>               165                 170               175 | 528 |
| atc tta ctc aga gct gca aat acc cac agt tcc gcc aaa cct tgc ggg<br>Ile Leu Leu Arg Ala Ala Asn Thr His Ser Ser Ala Lys Pro Cys Gly<br>180                       185                 190 | 576 |
| caa caa tcc att cac ttg gga gga gta ttt gaa ttg caa caa ggt gct<br>Gln Gln Ser Ile His Leu Gly Gly Val Phe Glu Leu Gln Gln Gly Ala<br>               195                 200               205 | 624 |
| tcg gtg ttt gtc aat gtg act gat cca agc caa gtg agc cat ggc act<br>Ser Val Phe Val Asn Val Thr Asp Pro Ser Gln Val Ser His Gly Thr<br>210                       215                 220 | 672 |
| ggc ttc acg tcc ttt ggc tta ctc aaa ctc tga gcggccgc<br>Gly Phe Thr Ser Phe Gly Leu Leu Lys Leu<br>225                       230 | 713 |

<210> SEQ ID NO 10
<211> LENGTH: 234
<212> TYPE: PRT
<213> ORGANISM: Homo sapiens

<400> SEQUENCE: 10

Met Ala Thr Gly Ser Arg Thr Ser Leu Leu Leu Ala Phe Gly Leu Leu
1                  5                      10                    15

Cys Leu Pro Trp Leu Gln Glu Gly Ser Ala Thr Arg Ser Asp Ile Leu
                  20                      25                      30

Leu Gln Leu Ser Thr Leu Phe Ser Ser Val Gln Gly His Gly Asn Ala
                      35                      40                    45

Ile Asp Glu Ile Ser Lys Ser Leu Ile Ser Leu Asn Thr Thr Leu Leu
        50                      55                      60

Asp Leu Gln Leu Asn Ile Glu Asn Leu Asn Gly Lys Ile Gln Ser Ser
65                  70                    75                    80

Pro Gly Ala Leu Glu Met Gln Lys Gly Asp Gln Asn Pro Gln Ile Ala
                      85                      90                    95

Ala His Val Ile Ser Glu Ala Ser Ser Lys Thr Thr Ser Val Leu Gln

-continued

```
            100                 105                 110
Trp Ala Glu Lys Gly Tyr Tyr Thr Met Ser Asn Asn Leu Val Thr Leu
            115                 120                 125

Glu Asn Gly Lys Gln Leu Thr Val Lys Arg Gln Gly Leu Tyr Tyr Ile
        130                 135                 140

Tyr Ala Gln Val Thr Phe Cys Ser Asn Arg Glu Ala Ser Ser Gln Ala
145                 150                 155                 160

Pro Phe Ile Ala Ser Leu Trp Leu Lys Ser Pro Gly Arg Phe Glu Arg
                165                 170                 175

Ile Leu Leu Arg Ala Ala Asn Thr His Ser Ser Ala Lys Pro Cys Gly
            180                 185                 190

Gln Gln Ser Ile His Leu Gly Gly Val Phe Glu Leu Gln Gln Gly Ala
        195                 200                 205

Ser Val Phe Val Asn Val Thr Asp Pro Ser Gln Val Ser His Gly Thr
    210                 215                 220

Gly Phe Thr Ser Phe Gly Leu Leu Lys Leu
225                 230
```

What is claimed is:

1. A fusion polypeptide comprising a first polypeptide consisting of amino acids x to y of the polypeptide depicted in SEQ ID NO: 10, wherein x is selected from positions 110 to 173 of SEQ ID NO: 10 andy is selected from positions 179 to 270 of SEQ ID NO: 10, fused to a second heterologous polypeptide, and wherein to fusion polypeptide is capable of forming a trimer.

2. A fusion polypeptide comprising a first polypeptide fused to a second, heterologous polypeptide, wherein
   the first polypeptide consists of amino acids x to y of the polypeptide depicted in SEQ ID NO: 10, wherein x is selected from positions 110 to 173 of SEQ ID NO: 10 and y is selected from positions 179 to 270 of SEQ ID NO: 10, with at least one substitution of an amino acid,
   the amino acid sequence of the first polypeptide is at least 80% identical over its length to the amino acid sequence of the polypeptide depicted in SEQ ID NO: 10 from positions x to y of SEQ ID NO: 10, and
   the fusion polypeptide is capable of forming a trimer.

3. A fusion polypeptide comprising a first polypeptide consisting of amino acids 154 to 203 of the polypeptide depicted in SEQ ID NO: 10, fused to a second heterologous polypeptide, wherein to fusion polypeptide is capable of forming a trimer.

4. The fusion polypeptide of claim 1, 2 or 3, wherein the second polypeptide is a soluble portion of a tumor necrosis factor receptor super family (TNFRSF).

5. The fusion polypeptide of claim 4, wherein the second polypeptide is a soluble portion of a tumor necrosis factor super family (INFSF) ligand.

6. The fusion polypeptide of claim 5, wherein the second polypeptide is a soluble portion of a polypeptide selected from the group of tumor necrosis factor receptor super family polypeptides consisting of TNFRSF1A, TNFRSF1B, TNFRSF3, TNFRSF4, TNFRSF5, TNFRSF6, TNFRSF6B, TNFRSF7, TNFRSF8, TNFRSF9, TNFRSF10A, TNFRSF10B, TNFRSF10C, TNFRSF10D, TNFRSF11A, TNFRSF11B, TNFRSF12, TNFRSF13B, TNFRSF14, TNFRSF16, TNFRSF17, TNFRSF18 and TNFRSF19.

7. The fusion polypeptide of claim 6, wherein the fusion polypeptide is capable of inhibiting signaling of a receptor from the tumor necrosis family receptor super family.

8. The fusion polypeplide of claim 7, wherein said first and second polypeptides of said fusion polypeptide are encoded by nucleic acids derived from a human.

9. The fusion polypeptide of claim 8, wherein said fusion polypeptide has reduced immunogenicity in humans.

10. The fusion polypeptide of claim 5, wherein the second polypeptide is a soluble portion of a polypeptide selected from the group consisting of TNFSF1, TNFSF2, TNFSF3, TNFSF4, TNFSF5, TNFSF6, TNFSF7, TNFSF8, TNFSF9, TNFSF10, TNFSF11, TNFSF12, TNFSF13, TNFSF14, TNFSF15, and TNFSF18.

11. The fusion polypeptide of claim 10, wherein the fusion polypeptide is capable of enhancing signaling of a receptor from the tumor necrosis family receptor super family.

12. The fusion polypeptide of claim 11, wherein said first and second polypeptides of said fusion polypeptide are encoded by nucleic acids derived from a human.

13. The fusion polypeptide of claim 12, wherein said fusion polypeptide is capable of forming a multimer of a trimer.

14. The fusion polypeptide of claim 13, wherein the second heterologous polypeptide comprises the amino acids depicted as amino acids 96 to 244 of SEQ ID NO:6.

15. A nucleic acid encoding the fusion polypeptide of any one of claims 1, 2 or 3.

16. An isolated host cell comprising a nucleic acid of claim 15, wherein said nucleic acid is operably linked to a heterologous control element.

17. An isolated host cell transfected with a nucleic acid according to claim 15.

18. A method of producing a fusion polypeptide encoded by the nucleic acid of claim 15, comprising the steps of growing a host cell transfected with said nucleic acid in conditions favorable for expression of the fusion polypeptide, and isolating said fusion polypeptide.

19. A recombinant vector comprising the nucleic acid of claim 15.

20. A method of constructing a recombinant expression vector encoding a fusion protein comprising the steps of inserting, into a compatible cloning site of an expression vector, a first nucleic acid consisting of nucleotides x to y of the nucleic acid depicted in SEQ ID NO:9, wherein x is selected from positions 331 to 508 of SEQ ID NO: 9, and y is selected from positions 546 to 808 of SEQ ID NO: 9, linked to a second nucleic acid encoding a heterologous polypeptide, followed by amplifying and isolating said recombinant expression vector, wherein the fusion protein encoded by the vector is capable of forming a trimer.

21. The method of claim 20, wherein the second nucleic acid encodes a soluble portion of a polypeptide selected from the group consisting of TNFSF1, TNFRSF1A, TNFSF2, TNFRSF1B, TNFSF3, TNFRSF3, TNFSF4, TNFRSF4, TNFSF5, TNFRSF5, TNFSF6, TNFRSF6, TNFRSF6B, TNFSF7, TNFRSF7, TNFSF8, TNFRSF8, TNFSF9, TNFRSF9, TNFSF10, TNFRSF10A, TNFRSF10B, TNFRSF10C, TNFRSF10D, TNFSF11, TNFRSF11A, TNFRSF11B, TNFSF12, TNFRSF12, TNFSF13, TNFRSF13B, TNFSF14, TNFRSF14, TNFSF15, TNFRSF16, TNFRSF17, TNFSF18, TNFRSF18, and TNFRSF 19.

* * * * *

UNITED STATES PATENT AND TRADEMARK OFFICE
CERTIFICATE OF CORRECTION

| | | |
|---|---|---|
| PATENT NO. | : 7,238,499 B2 | |
| APPLICATION NO. | : 10/326186 | |
| DATED | : July 3, 2007 | |
| INVENTOR(S) | : Pranhitha Reddy | |

It is certified that error appears in the above-identified patent and that said Letters Patent is hereby corrected as shown below:

In the Drawings:

At Sheet 5, delete Fig. 4.

In the Specification:

At Column 3, line 23, "y nucleotides is" should be -- y is nucleotides --.

At Column 3, line 37, "SEO" should be -- SEQ --.

At Column 5, line 1, "it's" should be -- its --.

At Column 5, line 4, "polypeptide the" should be -- polypeptide of the --.

At Column 6, line 29, ".edul" should be -- .edu/ --.

At Column 7, line 59, "4-2BB-L" should be -- 4-1-BB-L --.

At Column 12, line 33, "B1Ocore" should be -- BIOcore --.

Signed and Sealed this
Twenty-first Day of June, 2011

David J. Kappos
*Director of the United States Patent and Trademark Office*

CERTIFICATE OF CORRECTION (continued)
U.S. Pat. No. 7,238,499 B2

In the Sequence Listings:

At Column 17, SEQ ID NOs 5-10 should be replaced with the following SEQ ID NOs 5-11:

```
<210>  5
<211>  743
<212>  DNA
<213>  Homo sapiens

<220>
<221>  CDS
<222>  (1)..(735)
<223>

<400>  5
atg gcc ctg tgg atc gac agg atg caa ctc ctg tct tgc att gca cta      48
Met Ala Leu Trp Ile Asp Arg Met Gln Leu Leu Ser Cys Ile Ala Leu
1               5                   10                  15 agt ctt gca ctt gtc aca aac agt gca cct act tca agt tct aca aag      96
Ser Leu Ala Leu Val Thr Asn Ser Ala Pro Thr Ser Ser Ser Thr Lys
                20                  25                  30 aaa aca cag cta act agg tct gac att ctt ctg cag cta agt acc ttg     144
Lys Thr Gln Leu Thr Arg Ser Asp Ile Leu Leu Gln Leu Ser Thr Leu
            35                  40                  45 ttt tcc tca gtc cag gga cat ggg aat gca ata gat gaa atc tcc aag     192
Phe Ser Ser Val Gln Gly His Gly Asn Ala Ile Asp Glu Ile Ser Lys
        50                  55                  60 tcc tta ata agt ttg aat acc aca ttg ctt gat ttg cag ctc aac ata     240
Ser Leu Ile Ser Leu Asn Thr Thr Leu Leu Asp Leu Gln Leu Asn Ile
65                  70                  75                  80 gaa aat ctg aat ggc aaa atc caa tct tca cca gga gct cta gaa atg     288
Glu Asn Leu Asn Gly Lys Ile Gln Ser Ser Pro Gly Ala Leu Glu Met
                85                  90                  95 caa aaa ggt gat cag aat cct caa att gcg gca cat gtc ata agt gag     336
Gln Lys Gly Asp Gln Asn Pro Gln Ile Ala Ala His Val Ile Ser Glu
            100                 105                 110 gcc agc agt aaa aca aca tct gtg tta cag tgg gct gaa aaa gga tac     384
Ala Ser Ser Lys Thr Thr Ser Val Leu Gln Trp Ala Glu Lys Gly Tyr
        115                 120                 125 tac acc atg agc aac aac ttg gta acc ctg gaa aat ggg aaa cag ctg     432
Tyr Thr Met Ser Asn Asn Leu Val Thr Leu Glu Asn Gly Lys Gln Leu
130                 135                 140
```

```
acc gtt aaa aga caa gga ctc tat tat atc tat gcc caa gtc acc ttc      480
Thr Val Lys Arg Gln Gly Leu Tyr Tyr Ile Tyr Ala Gln Val Thr Phe
145                 150                 155                 160 tgt tcc aat cgg gaa gct tcg agt caa gct cca ttt ata gcc agc ctc      528
Cys Ser Asn Arg Glu Ala Ser Ser Gln Ala Pro Phe Ile Ala Ser Leu
                165                 170                 175 tgg cta aag tcc ccc ggt aga ttc gag aga atc tta ctc aga gct gca      576
Trp Leu Lys Ser Pro Gly Arg Phe Glu Arg Ile Leu Leu Arg Ala Ala
            180                 185                 190 aat acc cac agt tcc gcc aaa cct tgc ggg caa caa tcc att cac ttg      624
Asn Thr His Ser Ser Ala Lys Pro Cys Gly Gln Gln Ser Ile His Leu
        195                 200                 205 gga gga gta ttt gaa ttg caa cca ggt gct tcg gtg ttt gtc aat gtg      672
Gly Gly Val Phe Glu Leu Gln Pro Gly Ala Ser Val Phe Val Asn Val
    210                 215                 220 act gat cca agc caa gtg agc cat ggc act ggc ttc acg tcc ttt ggc      720
Thr Asp Pro Ser Gln Val Ser His Gly Thr Gly Phe Thr Ser Phe Gly
225                 230                 235                 240 tta ctc aaa ctc tga gcggccgc                                         743
Leu Leu Lys Leu <210>  6
<211>  244
<212>  PRT
<213>  Homo sapiens

<400>  6

Met Ala Leu Trp Ile Asp Arg Met Gln Leu Leu Ser Cys Ile Ala Leu
1               5                   10                  15

Ser Leu Ala Leu Val Thr Asn Ser Ala Pro Thr Ser Ser Ser Thr Lys
                20                  25                  30

Lys Thr Gln Leu Thr Arg Ser Asp Ile Leu Leu Gln Leu Ser Thr Leu
            35                  40                  45

Phe Ser Ser Val Gln Gly His Gly Asn Ala Ile Asp Glu Ile Ser Lys
        50                  55                  60

Ser Leu Ile Ser Leu Asn Thr Thr Leu Leu Asp Leu Gln Leu Asn Ile
```

```
          65                      70                      75                      80

Glu Asn Leu Asn Gly Lys Ile Gln Ser Ser Pro Gly Ala Leu Glu Met
                      85                  90                  95

Gln Lys Gly Asp Gln Asn Pro Gln Ile Ala Ala His Val Ile Ser Glu
                     100                 105                 110

Ala Ser Ser Lys Thr Thr Ser Val Leu Gln Trp Ala Glu Lys Gly Tyr
                 115                 120                 125

Tyr Thr Met Ser Asn Asn Leu Val Thr Leu Glu Asn Gly Lys Gln Leu
             130                 135                 140

Thr Val Lys Arg Gln Gly Leu Tyr Tyr Ile Tyr Ala Gln Val Thr Phe
     145                 150                 155                 160

Cys Ser Asn Arg Glu Ala Ser Ser Gln Ala Pro Phe Ile Ala Ser Leu
                     165                 170                 175

Trp Leu Lys Ser Pro Gly Arg Phe Glu Arg Ile Leu Leu Arg Ala Ala
                 180                 185                 190

Asn Thr His Ser Ser Ala Lys Pro Cys Gly Gln Gln Ser Ile His Leu
             195                 200                 205

Gly Gly Val Phe Glu Leu Gln Pro Gly Ala Ser Val Phe Val Asn Val
             210                 215                 220

Thr Asp Pro Ser Gln Val Ser His Gly Thr Gly Phe Thr Ser Phe Gly
     225                 230                 235                 240

Leu Leu Lys Leu

<210> 7
     <211> 713
     <212> DNA
     <213> Homo sapiens

<220>
```

```
<221>  CDS
<222>  (1)..(705)
<223>

<400>  7
atg gct aca ggc tcc cgg acg tcc ctg ctc ctg gct ttt ggc ctg ctc      48
Met Ala Thr Gly Ser Arg Thr Ser Leu Leu Leu Ala Phe Gly Leu Leu
1               5                   10                  15 tgc ctg ccc tgg ctt caa gag ggc agt gca act agg tct gac att ctt      96
Cys Leu Pro Trp Leu Gln Glu Gly Ser Ala Thr Arg Ser Asp Ile Leu
            20                  25                  30 ctg cag cta agt acc ttg ttt tcc tca gtc cag gga cat ggg aat gca     144
Leu Gln Leu Ser Thr Leu Phe Ser Ser Val Gln Gly His Gly Asn Ala
        35                  40                  45 ata gat gaa atc tcc aag tcc tta ata agt ttg aat acc aca ttg ctt     192
Ile Asp Glu Ile Ser Lys Ser Leu Ile Ser Leu Asn Thr Thr Leu Leu
    50                  55                  60 gat ttg cag ctc aac ata gaa aat ctg aat ggc aaa atc caa tct tca     240
Asp Leu Gln Leu Asn Ile Glu Asn Leu Asn Gly Lys Ile Gln Ser Ser
65                  70                  75                  80 cca gga gct cta gaa atg caa aaa ggt gat cag aat cct caa att gcg     288
Pro Gly Ala Leu Glu Met Gln Lys Gly Asp Gln Asn Pro Gln Ile Ala
                85                  90                  95 gca cat gtc ata agt gag gcc agc agt aaa aca aca tct gtg tta cag     336
Ala His Val Ile Ser Glu Ala Ser Ser Lys Thr Thr Ser Val Leu Gln
            100                 105                 110 tgg gct gaa aaa gga tac tac acc atg agc aac aac ttg gta acc ctg     384
Trp Ala Glu Lys Gly Tyr Tyr Thr Met Ser Asn Asn Leu Val Thr Leu
        115                 120                 125 gaa aat ggg aaa cag ctg acc gtt aaa aga caa gga ctc tat tat atc     432
Glu Asn Gly Lys Gln Leu Thr Val Lys Arg Gln Gly Leu Tyr Tyr Ile
    130                 135                 140 tat gcc caa gtc acc ttc tgt tcc aat cgg gaa gct tcg agt caa gct     480
Tyr Ala Gln Val Thr Phe Cys Ser Asn Arg Glu Ala Ser Ser Gln Ala
145                 150                 155                 160 cca ttt ata gcc agc ctc tgg cta aag tcc ccc ggt aga ttc gag aga     528
Pro Phe Ile Ala Ser Leu Trp Leu Lys Ser Pro Gly Arg Phe Glu Arg
                165                 170                 175 atc tta ctc aga gct gca aat acc cac agt tcc gcc aaa cct tgc ggg     576
Ile Leu Leu Arg Ala Ala Asn Thr His Ser Ser Ala Lys Pro Cys Gly
            180                 185                 190
```

```
caa caa tcc att cac ttg gga gga gta ttt gaa ttg caa caa ggt gct      624
Gln Gln Ser Ile His Leu Gly Gly Val Phe Glu Leu Gln Gln Gly Ala
            195                 200                 205 tcg gtg ttt gtc aat gtg act gat cca agc caa gtg agc cat ggc act      672
Ser Val Phe Val Asn Val Thr Asp Pro Ser Gln Val Ser His Gly Thr
    210                 215                 220 ggc ttc acg tcc ttt ggc tta ctc aaa ctc tga gcggccgc                 713
Gly Phe Thr Ser Phe Gly Leu Leu Lys Leu
225                 230
```

<210> 8
<211> 234
<212> PRT
<213> Homo sapiens

<400> 8

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Thr Arg Ser Asp Ile Leu
                20                  25                  30

Leu Gln Leu Ser Thr Leu Phe Ser Ser Val Gln Gly His Gly Asn Ala
            35                  40                  45

Ile Asp Glu Ile Ser Lys Ser Leu Ile Ser Leu Asn Thr Thr Leu Leu
        50                  55                  60

Asp Leu Gln Leu Asn Ile Glu Asn Leu Asn Gly Lys Ile Gln Ser Ser
65                  70                  75                  80

Pro Gly Ala Leu Glu Met Gln Lys Gly Asp Gln Asn Pro Gln Ile Ala
                85                  90                  95

Ala His Val Ile Ser Glu Ala Ser Ser Lys Thr Thr Ser Val Leu Gln
            100                 105                 110

Trp Ala Glu Lys Gly Tyr Tyr Thr Met Ser Asn Asn Leu Val Thr Leu
        115                 120                 125

```
Glu Asn Gly Lys Gln Leu Thr Val Lys Arg Gln Gly Leu Tyr Tyr Ile
    130                 135                 140

Tyr Ala Gln Val Thr Phe Cys Ser Asn Arg Glu Ala Ser Ser Gln Ala
145                 150                 155                 160

Pro Phe Ile Ala Ser Leu Trp Leu Lys Ser Pro Gly Arg Phe Glu Arg
                165                 170                 175

Ile Leu Leu Arg Ala Ala Asn Thr His Ser Ser Ala Lys Pro Cys Gly
                180                 185                 190

Gln Gln Ser Ile His Leu Gly Gly Val Phe Glu Leu Gln Gln Gly Ala
            195                 200                 205

Ser Val Phe Val Asn Val Thr Asp Pro Ser Gln Val Ser His Gly Thr
    210                 215                 220

Gly Phe Thr Ser Phe Gly Leu Leu Lys Leu
225                 230

<210>  9
<211>  1077
<212>  DNA
<213>  Homo sapiens

<220>
<221>  CDS
<222>  (1)..(1077)
<223>

<400>  9
atg gag cag tgg gat cac ttt cac aat caa cag gag gac act gat agc      48
Met Glu Gln Trp Asp His Phe His Asn Gln Gln Glu Asp Thr Asp Ser
1               5                   10                  15 tgc tcc gaa tct gtg aaa ttt gat gct cgc tca atg aca gct ttg ctt      96
Cys Ser Glu Ser Val Lys Phe Asp Ala Arg Ser Met Thr Ala Leu Leu
                20                  25                  30 cct ccg aat cct aaa aac agc cct tcc ctt caa gag aaa ctg aag tcc     144
Pro Pro Asn Pro Lys Asn Ser Pro Ser Leu Gln Glu Lys Leu Lys Ser
            35                  40                  45 ttc aaa gct gca ctg att gcc ctt tac ctc ctc gtg ttt gca gtt ctc     192
```

```
                Phe Lys Ala Ala Leu Ile Ala Leu Tyr Leu Leu Val Phe Ala Val Leu
                    50                  55                  60 atc cct ctc att gga ata gtg gca gct caa ctc ctg aag tgg gaa acg        240
Ile Pro Leu Ile Gly Ile Val Ala Ala Gln Leu Leu Lys Trp Glu Thr
65                  70                  75                  80 aag aat tgc tca gtt agt tca act aat gca aat gat ata act caa agt        288
Lys Asn Cys Ser Val Ser Ser Thr Asn Ala Asn Asp Ile Thr Gln Ser
                85                  90                  95 ctc acg gga aaa gga aat gac agc gaa gag gaa atg aga ttt caa gaa        336
Leu Thr Gly Lys Gly Asn Asp Ser Glu Glu Glu Met Arg Phe Gln Glu
            100                 105                 110 gtc ttt atg gaa cac atg agc aac atg gag aag aga atc cag cat att        384
Val Phe Met Glu His Met Ser Asn Met Glu Lys Arg Ile Gln His Ile
        115                 120                 125 tta gac atg gaa gcc aac ctc atg gac aca gag cat ttc caa aat ttc        432
Leu Asp Met Glu Ala Asn Leu Met Asp Thr Glu His Phe Gln Asn Phe
    130                 135                 140 agc atg aca act gat caa aga ttt aat gac att ctt ctg cag cta agt        480
Ser Met Thr Thr Asp Gln Arg Phe Asn Asp Ile Leu Leu Gln Leu Ser
145                 150                 155                 160 acc ttg ttt tcc tca gtc cag gga cat ggg aat gca ata gat gaa atc        528
Thr Leu Phe Ser Ser Val Gln Gly His Gly Asn Ala Ile Asp Glu Ile
                165                 170                 175 tcc aag tcc tta ata agt ttg aat acc aca ttg ctt gat ttg cag ctc        576
Ser Lys Ser Leu Ile Ser Leu Asn Thr Thr Leu Leu Asp Leu Gln Leu
            180                 185                 190 aac ata gaa aat ctg aat ggc aaa atc caa gag aat acc ttc aaa caa        624
Asn Ile Glu Asn Leu Asn Gly Lys Ile Gln Glu Asn Thr Phe Lys Gln
        195                 200                 205 caa gag gaa atc agt aaa tta gag gag cgt gtt tac aat gta tca gca        672
Gln Glu Glu Ile Ser Lys Leu Glu Glu Arg Val Tyr Asn Val Ser Ala
    210                 215                 220 gaa att atg gct atg aaa gaa gaa caa gtg cat ttg gaa cag gaa ata        720
Glu Ile Met Ala Met Lys Glu Glu Gln Val His Leu Glu Gln Glu Ile
225                 230                 235                 240 aaa gga gaa gtg aaa gta ctg aat aac atc act aat gat ctc aga ctg        768
Lys Gly Glu Val Lys Val Leu Asn Asn Ile Thr Asn Asp Leu Arg Leu
                245                 250                 255 aaa gat tgg gaa cat tct cag acc ttg aga aat atc act tta att caa        816
```

```
       Lys Asp Trp Glu His Ser Gln Thr Leu Arg Asn Ile Thr Leu Ile Gln
               260                 265                 270 ggt cct cct gga ccc ccg ggt gaa aaa gga gat cga ggt ccc act gga        864
Gly Pro Pro Gly Pro Pro Gly Glu Lys Gly Asp Arg Gly Pro Thr Gly
        275                 280                 285 gaa agt ggt cca cga gga ttt cca ggt cca ata ggt cct ccg ggt ctt        912
Glu Ser Gly Pro Arg Gly Phe Pro Gly Pro Ile Gly Pro Pro Gly Leu
        290                 295                 300 aaa ggt gat cgg gga gca att ggc ttt cct gga agt cga gga ctc cca        960
Lys Gly Asp Arg Gly Ala Ile Gly Phe Pro Gly Ser Arg Gly Leu Pro
305                 310                 315                 320 gga tat gcc gga agg cca gga aat tct gga cca aaa ggc cag aaa ggg       1008
Gly Tyr Ala Gly Arg Pro Gly Asn Ser Gly Pro Lys Gly Gln Lys Gly
                325                 330                 335 gaa aag ggg agt gga aac aca tta aga cca gta caa ctc act gat cat       1056
Glu Lys Gly Ser Gly Asn Thr Leu Arg Pro Val Gln Leu Thr Asp His
                340                 345                 350
att agg gca ggg ccc tct taa                                            1077
Ile Arg Ala Gly Pro Ser
        355

<210> 10
<211> 358
<212> PRT
<213> Homo sapiens

<400> 10

Met Glu Gln Trp Asp His Phe His Asn Gln Gln Glu Asp Thr Asp Ser
1               5                   10                  15

Cys Ser Glu Ser Val Lys Phe Asp Ala Arg Ser Met Thr Ala Leu Leu
                20                  25                  30

Pro Pro Asn Pro Lys Asn Ser Pro Ser Leu Gln Glu Lys Leu Lys Ser
                35                  40                  45

Phe Lys Ala Ala Leu Ile Ala Leu Tyr Leu Leu Val Phe Ala Val Leu
        50                  55                  60

Ile Pro Leu Ile Gly Ile Val Ala Ala Gln Leu Leu Lys Trp Glu Thr
65                  70                  75                  80
```

```
Lys Asn Cys Ser Val Ser Ser Thr Asn Ala Asn Asp Ile Thr Gln Ser
                85              90              95

Leu Thr Gly Lys Gly Asn Asp Ser Glu Glu Glu Met Arg Phe Gln Glu
            100             105             110

Val Phe Met Glu His Met Ser Asn Met Glu Lys Arg Ile Gln His Ile
        115             120             125

Leu Asp Met Glu Ala Asn Leu Met Asp Thr Glu His Phe Gln Asn Phe
    130             135             140

Ser Met Thr Thr Asp Gln Arg Phe Asn Asp Ile Leu Leu Gln Leu Ser
145             150             155             160

Thr Leu Phe Ser Ser Val Gln Gly His Gly Asn Ala Ile Asp Glu Ile
            165             170             175

Ser Lys Ser Leu Ile Ser Leu Asn Thr Thr Leu Leu Asp Leu Gln Leu
        180             185             190

Asn Ile Glu Asn Leu Asn Gly Lys Ile Gln Glu Asn Thr Phe Lys Gln
    195             200             205

Gln Glu Glu Ile Ser Lys Leu Glu Glu Arg Val Tyr Asn Val Ser Ala
    210             215             220

Glu Ile Met Ala Met Lys Glu Glu Gln Val His Leu Glu Gln Glu Ile
225             230             235             240

Lys Gly Glu Val Lys Val Leu Asn Asn Ile Thr Asn Asp Leu Arg Leu
            245             250             255

Lys Asp Trp Glu His Ser Gln Thr Leu Arg Asn Ile Thr Leu Ile Gln
            260             265             270

Gly Pro Pro Gly Pro Pro Gly Glu Lys Gly Asp Arg Gly Pro Thr Gly
        275             280             285
```

```
    Glu Ser Gly Pro Arg Gly Phe Pro Gly Pro Ile Gly Pro Pro Gly Leu
        290                 295                 300

Lys Gly Asp Arg Gly Ala Ile Gly Phe Pro Gly Ser Arg Gly Leu Pro
    305                 310                 315                 320

Gly Tyr Ala Gly Arg Pro Gly Asn Ser Gly Pro Lys Gly Gln Lys Gly
                    325                 330                 335

Glu Lys Gly Ser Gly Asn Thr Leu Arg Pro Val Gln Leu Thr Asp His
                340                 345                 350

Ile Arg Ala Gly Pro Ser
                355

<210>   11
<211>   174
<212>   DNA
<213>   Homo sapiens

<400>   11
ctaggtctga cattcttctg cagctaagta ccttgttttc ctcagtccag ggacatggga      60
atgcaataga tgaaatctcc aagtccttaa taagtttgaa taccacattg cttgatttgc     120
agctcaacat agaaaatctg aatggcaaaa tccaatcttc accaggagct ctag           174
```

In the Claims:

At Column 29, line 58, "(INFSF)" should be -- (TNFSF) --.

At Column 31, lines 1-11 (claim 20), "A method of constructing a recombinant expression vector encoding a fusion protein comprising the steps of inserting, into a compatible cloning site of an expression vector, a first nucleic acid consisting of nucleotides x to y of the nucleic acid depicted in SEQ ID NO: 9, wherein x is selected from positions 331 to 508 of SEQ ID NO: 9, and y is selected from positions 546 to 808 of SEQ ID NO: 9, linked to a second nucleic acid encoding a heterologous polypeptide, followed by amplifying and isolating said recombinant expression vector, wherein the fusion protein encoded by the vector is capable of forming a trimer." should be -- A method of constructing a recombinant expression vector comprising the steps of linking a first nucleic acid comprising nucleotides x to y of the nucleic acid depicted in SEQ ID NO: 9, wherein x is selected from positions 331 to 508 of SEQ ID NO: 9, and y is selected from positions 546 to 808 of SEQ ID NO: 9, and a second nucleic acid encoding a heterologous polypeptide to the first nucleic acid into a compatible cloning site of an expression vector, followed by amplifying and isolating said recombinant expression vector. --.

CERTIFICATE OF CORRECTION (continued)
U.S. Pat. No. 7,238,499 B2

At Column 32, lines 7-11 (claim 21), "TNFRSF12, TNFSF13, TNFRSF13B, TNFSF14, TNFRS14, TNFSF15, TNFRSF16, TNFRSF17, TNFS18, TNFRS18, and TNFRSF 19." should be -- TNFRSF12, TNFRSF12L, TNFSF13, TNFRSF13, TNFRSF13B, TNFSF14, TNFRS14, TNFSF15, TNFRSF15, TNSF16, TNFRSF16, TNFSF17, TNFRSF17, TNFSF18, TNFRSF18, TNFSF19, TNFRSF19, TNFSF20, and TNFRSF20. --.